United States Patent
Weber et al.

(10) Patent No.: US 10,392,324 B2
(45) Date of Patent: Aug. 27, 2019

(54) XYLENE SEPARATION PROCESS

(71) Applicants: EXXONMOBIL CHEMICAL PATENTS INC., Baytown, TX (US); GEORGIA TECH RESEARCH CORPORATION, Atlanta, GA (US)

(72) Inventors: Michael W. Weber, Houston, TX (US); Yoshiaki Kawajiri, Nagoya (JP); Michael Salciccioli, Houston, TX (US); John R. Porter, Lake Michigan, MI (US); Gaurav Agrawal, Raritan, NJ (US); Dana L. Pilliod, League City, TX (US); Siwei Guo, Atlanta, GA (US); Jason Bentley, Duluth, GA (US)

(73) Assignees: EXXONMOBIL CHEMICAL PATENTS INC., Baytown, TX (US); GEORGIA TECH RESEARCH CORPORATION, Atlanta, GA (US)

( * ) Notice: Subject to any disclaimer, the term of this patent is extended or adjusted under 35 U.S.C. 154(b) by 0 days.

(21) Appl. No.: 16/097,734

(22) PCT Filed: May 17, 2017

(86) PCT No.: PCT/US2017/033096
§ 371 (c)(1),
(2) Date: Oct. 30, 2018

(87) PCT Pub. No.: WO2017/201159
PCT Pub. Date: Nov. 23, 2017

(65) Prior Publication Data
US 2019/0185394 A1 Jun. 20, 2019

Related U.S. Application Data

(60) Provisional application No. 62/339,286, filed on May 20, 2016.

(51) Int. Cl.
C07C 7/13 (2006.01)
B01D 53/08 (2006.01)
(Continued)

(52) U.S. Cl.
CPC ............... *C07C 7/13* (2013.01); *B01D 53/08* (2013.01); *C07C 15/073* (2013.01); *C07C 15/08* (2013.01);
(Continued)

(58) Field of Classification Search
None
See application file for complete search history.

(56) References Cited

U.S. PATENT DOCUMENTS 3,201,491 A 8/1965 Stine et al.
3,761,533 A 9/1973 Otani et al.
(Continued)

FOREIGN PATENT DOCUMENTS

WO 2016/133589 A1 8/2016

OTHER PUBLICATIONS

International Search Report and Written Opinion issued in the corresponding application No. PCT/US2017/033096 dated Jul. 27, 2017.
(Continued)

*Primary Examiner* — Tam M Nguyen
(74) *Attorney, Agent, or Firm* — Roberts Mlotkowski Safran Cole & Calderon, P.C.

(57) ABSTRACT

A process to separate paraxylene from a mixture of paraxylene, metaxylene, orthoxylene, and ethylbenzene in a commercial simulated moving bed apparatus in a reduced number of beds is provided, allowing an additional separation to be conducted in the remaining beds. This additional separation may separate another xylene isomer, ethylbenzene, or a non-aromatic $C_{8+}$ hydrocarbon from the raffinate stream
(Continued)

produced by the first separation. A PowerFeed process is used to recover paraxylene in a first adsorption zone containing 8-16 beds of a conventional 24-bed simulated moving bed adsorption apparatus, and then a second separation may be conducted in a second adsorption zone containing the remaining beds.

25 Claims, 6 Drawing Sheets

(51) Int. Cl.
  *C07C 15/08*  (2006.01)
  *C07C 15/073*  (2006.01)
  *B01J 20/16*  (2006.01)

(52) U.S. Cl.
  CPC ..... B01D 2257/7027 (2013.01); *B01J 20/165* (2013.01); *C07C 2529/08* (2013.01); *C07C 2529/40* (2013.01)

(56) References Cited

U.S. PATENT DOCUMENTS

| | | |
|---|---|---|
| 4,029,717 A | 6/1977 | Healy et al. |
| 4,313,015 A | 1/1982 | Broughton |
| 5,102,553 A | 4/1992 | Kearney et al. |
| 6,136,198 A | 10/2000 | Adam et al. |
| 8,168,845 B2 | 5/2012 | Porter et al. |
| 8,529,757 B2 | 9/2013 | Go et al. |
| 2009/0234170 A1 | 9/2009 | Lee et al. |
| 2010/0125163 A1 | 5/2010 | Porter et al. |
| 2013/0006031 A1 | 1/2013 | Leflaive et al. |
| 2013/0053610 A1 | 2/2013 | Leinekugel Le Cocq et al. |
| 2013/0233698 A1* | 9/2013 | Corradi ................. B01D 3/143 203/41 |
| 2014/0288345 A1* | 9/2014 | Corradi .................... C07C 7/12 585/828 |
| 2016/0145174 A1 | 5/2016 | Porter et al. |
| 2017/0239591 A1* | 8/2017 | Ou ..................... B01D 15/1828 |
| 2018/0009729 A1* | 1/2018 | Ou ........................ C07C 15/073 |

OTHER PUBLICATIONS

Kawajiri et al., "Optimization strategies for simulated moving bed and PowerFeed processes", AIChE J. vol. 52 (2006) 8, pp. 1343-1350.

Zhang et al., "PowerFeed operation of simulated moving bed units: changing flow-rates during the switching interval", Journal of Chromatography A. 1006, pp. 87-99, 2003, Elsevier B.V.

* cited by examiner

XYLENE SEPARATION PROCESS

CROSS-REFERENCE TO RELATED APPLICATIONS

The present application is a U.S. National Phase of PCT/US2017/033096 filed on May 17, 2017 claiming priority to provisional U.S. Patent Application No. 62/339,286 filed May 20, 2016. The disclosure of the PCT Application is hereby incorporated by reference into the present Application.

TECHNICAL FIELD

This disclosure relates to a process for separating paraxylene from a mixture comprising $C_8$ aromatics by means of a simulated moving bed adsorption apparatus using a PowerFeed process that allows for an additional separation of at least one of metaxylene, orthoxylene, ethylbenzene, or a non-aromatic.

BACKGROUND

Of the three xylene isomers, paraxylene is the most commercially valuable. Due to the similarity of their boiling points, adsorption, using an adsorbent solid which preferentially adsorbs paraxylene over metaxylene and orthoxylene in a simulated moving bed apparatus, is a common method for separating paraxylene from the other xylene isomers. A commercial embodiment of a simulated moving bed adsorption apparatus is used in the well-known Parex™ Process, which is used to separate $C_8$ aromatic isomers and provide a more highly pure paraxylene from a less highly pure mixture. See by way of example U.S. Pat. Nos. 3,201,491; 3,761,533; and 4,029,717. Other embodiments involving a simulated moving bed adsorption apparatus include ELUXYL™, available from Axens, and AROMAX™, available from Toray.

In a Parex™ unit, the locations of liquid input and output are moved by a fluid directing device. This fluid directing device may comprise one or more rotary valves, as well as various control and accessory means, such as inlet lines, outlets lines, and valves associated therewith. The fluid directing device works in conjunction with conduits connected to adsorbent beds. The fluid directing device accomplishes moving the input and output locations through first directing the liquid introduction or withdrawal lines to specific conduits in fluid communication with particular adsorbent beds. After a specified time period, called the step time, the fluid directing device advances one index and redirects the liquid inputs and outputs to the conduit immediately adjacent and downstream of the previously used conduits. Each advancement of the fluid directing device to a new position is generally called a valve step, and the completion of all the valve steps is called a valve cycle. The step time or step interval is uniform for each valve step in a valve cycle, and may be from about 30 seconds to 4 minutes.

Commercial simulated moving bed adsorption apparatuses such as Parex™ or ELUXYL™ typically contain 24 adsorbent beds and 24 conduits individually connected to a bed and providing fluid communication with the fluid directing device. The conduits of the adsorption apparatus may function, over time, as at least two liquid input lines (e.g., a feed input line and a desorbent input line) and two liquid output lines (e.g., an extract withdrawal line and a reformate withdrawal line).

Systems employing a simulated countercurrent flow process are described in U.S. Pat. Nos. 3,201,491; 3,761,533; 4,029,717; and 8,529,757. Such systems generally include one or more distillation towers and attendant pumps and conduits, which may be utilized to purify the liquid withdrawal streams taken from adsorbent beds.

In standard simulated moving bed separation processes, the flow rate of streams into and out of the simulated moving bed are held constant during the step time. However, modulation of flow during the step time has been found to enhance separation in certain instances involving simulated moving bed separation of fructose and glucose or separation of 1,1'-bi-2-naphthol enatiomers. The enhanced separation may result in greater purity of product streams or less desorbent use. This process for modulating flow rates during a step time has been referred to as a PowerFeed process. Examples of PowerFeed processes are described in an article by Kawajiri et al., "Optimization strategies for simulated moving bed and PowerFeed processes," AIChE J. Vol. 52 (2006) B, pp. 1343-1350, and in an article by Zhang et al., "PowerFeed operation of simulated moving bed units: changing flow-rates during the switching interval," Journal of Chromatography A. 1006, pp. 87-99, 2003, Elsevier B.V. The use of PowerFeed operation to separate paraxylene from a mixture of $C_8$ aromatics in a simulated moving bed process is described in International Patent Application PCT/US2015/067701, filed Dec. 28, 2015.

There is an ongoing need to further improve the simulated moving bed adsorption process, maximize the purity of product streams and make the process more efficient. It would be desirable to reduce the number of beds in the unit, thereby reducing the number of conduits and connection devices needed to achieve proper flow of fluids into, out and through the beds of the simulated moving bed apparatus.

BRIEF SUMMARY

Embodiments disclosed herein utilize a PowerFeed process to effectively separate paraxylene from a mixture of paraxylene, metaxylene, orthoxylene, and ethylbenzene in a commercial simulated moving bed apparatus in a reduced number of beds, allowing an additional separation to be conducted in the remaining beds. This additional separation may separate another xylene isomer, ethylbenzene, or a non-aromatic hydrocarbon from the raffinate produced by the first separation.

In one embodiment, a process for separating paraxylene and at least one other $C_8$ aromatic from a mixture of paraxylene, metaxylene, orthoxylene, and ethylbenzene in simulated moving bed adsorption apparatus having 24 adsorbent beds is provided. The 24 adsorbent beds are arranged in two columns, with each column containing 12 adsorbent beds. The simulated moving bed adsorption apparatus comprises a first absorption zone containing 8 to 16 absorbent beds and a second absorption zone containing the balance of the 24 adsorbent beds. Each adsorption zone performs a different separation and may be contained in a single column or span both columns. The improvement the claimed process provides is separating paraxylene from the mixture in the first adsorption zone to produce a raffinate comprising metaxylene, orthoxylene, and ethylbenzene. The raffinate is then passed to the second adsorption zone where at least one of metaxylene, orthoxylene, and ethylbenzene is separated from the raffinate. A PowerFeed process is used in the first adsorption zone, meaning the flow rate of at least one of the first feed stream, first desorbent stream, first extract stream, or first raffinate stream introduced into or withdrawn from the first adsorption zone is varied during a step time interval X.

In another embodiment, paraxylene and at least one other $C_8$ aromatic is separated from a mixture comprising $C_8$ aromatics in a simulated moving bed adsorption apparatus comprising 24 adsorbent beds in two columns, each column containing 12 adsorbent beds. The simulated moving bed adsorption apparatus comprises a first adsorption zone, which contains between 8 and 16 adsorbent beds, and a second adsorption zone, which contains the remainder of the 24 adsorbent beds, each of which performs a different separation. The first and second adsorption zones may each be contained in a single column or span both columns. The number of adsorbent beds in the first adsorption zone may be 8, 12, or 16.

A first feed stream, which comprises a mixture of paraxylene, metaxylene, orthoxylene, and ethylbenzene, and a first desorbent stream, which comprises desorbent, are introduced into the first adsorption zone of the simulated moving bed adsorption apparatus. A first extract stream, which comprises desorbent and paraxylene, and a first raffinate stream, which comprises desorbent, metaxylene, orthoxylene, and ethylbenzene, are withdrawn from the first adsorption zone, and a flow of circulating fluid is maintained throughout the first adsorption zone. After a step time interval X, the flow of streams into and out of the first adsorption zone is switched to a bed downstream in terms of the direction of the circulating fluid. During step time interval X, the flow rate of at least one of the first feed stream, first desorbent stream, first extract stream, and first raffinate stream is varied.

A second feed stream, which comprises at least a portion of the first raffinate stream, and a second desorbent stream, which comprises desorbent, are introduced into the second adsorption zone. A second extract stream, which comprises desorbent and a $C_8$ aromatic selected from the group consisting of metaxylene, orthoxylene, and ethylbenzene, and a second raffinate stream, which comprises desorbent and the two $C_8$ aromatics not contained in the extract stream, are withdrawn from the second adsorption zone, and a flow of circulating fluid is maintained throughout the second adsorption zone. After a step time interval Y, which may be the same as or different than step time interval X, the flow of streams into and out of the second adsorption zone to a bed downstream in terms of the direction of the circulating fluid. The flow rate of at least one of the second feed stream, second desorbent stream, second extract stream, and second raffinate stream may or may not be varied during step time interval Y.

The present separation process may take place in a standard 24 bed simulated moving bed system, which has been retrofit to accommodate the flow of streams. For example, a standard 24 bed simulated moving bed system, such as a Parex™ unit, may be replumbed to provide two separation zones, instead of one separation zone. The standard 24 bed simulated moving bed system may also be retrofit to provide a separate flow of circulating bulk fluid through each of the first and second adsorption zones.

These and other objects, features, and advantages will become apparent in the following detailed description, drawings, specific embodiments, experiments, and accompanying claims.

DETAILED DESCRIPTION

Figure 1:
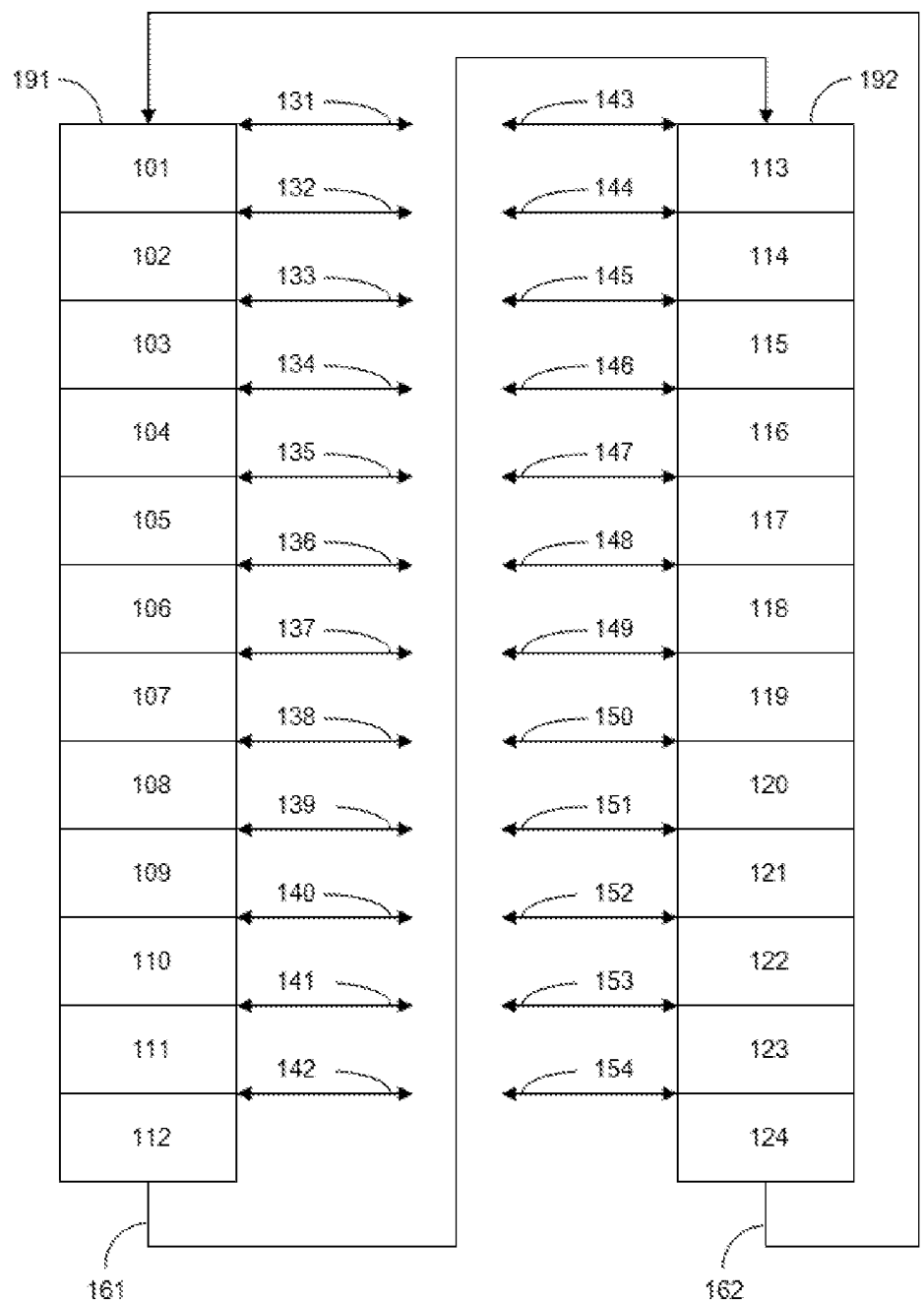
FIG. 1 is a schematic illustration of a simulated moving bed adsorptive separation system.

Embodiments disclosed herein utilize a PowerFeed process to effectively separate paraxylene from a mixture of paraxylene, metaxylene, orthoxylene, and ethylbenzene in a commercial simulated moving bed apparatus in a reduced number of beds, allowing an additional separation to be conducted in the remaining beds. This additional separation may separate another xylene isomer, ethylbenzene, or a non-aromatic $C_8$ hydrocarbon from the raffinate stream produced by the first separation.

Definitions

Various terms used in this description will be understood in the context of this description. A further explanation of certain terms used herein is provided below.

The term "$C_n$" hydrocarbon wherein n is a positive integer, means a hydrocarbon having n number of carbon atom(s) per molecule. The terms "$C_{n+}$" hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The term "aromatics" means hydrocarbon molecules containing at least one aromatic core. The term "hydrocarbon" encompasses mixtures of hydrocarbon, including those having different values of n. $C_8$ aromatics are aromatic compounds having 8 carbon atoms. Examples of $C_8$ aromatics include paraxylene, metaxylene, orthoxylene, and ethylbenzene.

Equilibrium xylene is a mixture of $C_8$ aromatics having a thermodynamic equilibrium concentration of the various $C_8$ aromatic compounds when the $C_8$ aromatics are subjected to non-selective isomerization conditions. Equilibrium xylene may be produced in a non-selective process for producing xylenes. A non-selective process for producing xylenes may involve reacting reactants over a non-selective catalyst. Equilibrium xylene may be produced, for example, in a xylene isomerization process, a transalkylation process, or a reforming process. Equilibrium xylene may also be produced by other processes. Equilibrium xylene may comprise, for example, about 23 percent paraxylene, based on the total of the xylenes.

Enhanced paraxylene is a mixture of $C_8$ aromatics having a greater concentration of paraxylene than equilibrium xylene. Enhanced paraxylene may be produced in a selective process for producing xylenes. A selective process for producing xylenes may involve reacting reactants over a selective catalyst. Enhanced paraxylene may be produced, for example, by a selective toluene disproportion process or a selective toluene alkylation process. Enhanced paraxylene may also be produced by other processes. Enhanced paraxylene may have a concentration of, for example, at least 75% paraxylene, based on the total of $C_8$ aromatics.

A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore size zeolite, equilibrium zeolites may be produced.

A selective process for producing paraxylene is a process which produces paraxylene in preference to other xylene isomers (metaxylene and orthoxylene). A selective process for producing paraxylene may be produced, for example, by a catalytic process over a paraxylene selective catalyst. Examples of paraxylene selective catalysts include medium pore size zeolites, such as ZSM-5, modified with selectivating agents. Selectivating agents may neutralize surface catalytic sites or narrow the pores of the catalyst. Examples of paraxylene selective catalysts and selectivating agents are provided by in U.S. Pat. Nos. 5,365,004 and 4,088,706 and International Publication No. WO 2013/330093.

Circulating bulk fluid is the fluid (i.e., liquid) which flows in a continuous manner through a simulated moving bed adsorption apparatus. The concentration of compounds in this circulating bulk fluid changes as this fluid flows through the apparatus due to, inter alia, adsorption and desorption of xylenes, ethylbenzene and desorbent, withdrawal of fluids in extract and reformate streams, and introduction of fluids through feed, desorbent and flush streams.

A liquid distribution device which distributes the flow of stream into and out of a simulated moving bed adsorptive separation device. A liquid distribution device may comprise a rotary valve or a system of other types of valves, such as the system used in the ELUXYL™ process.

A rotary valve device is a device comprising at least one rotary valve. The rotary valve device may comprise various control and accessory means, such as inlet lines, outlet lines and valves associated therewith.

A simulated moving bed adsorption apparatus is an apparatus including beds of adsorbent stacked in at least one column. In operative use of the adsorption apparatus, the beds are connected in a fluid and circular manner in series with one another.

A simulated countercurrent absorptive separation is a separation which takes place in a simulated moving bed adsorption apparatus.

An adsorbent column is an apparatus having adsorbent beds stacked one on top of the other.

An adsorbent bed chamber is a chamber in an adsorption apparatus containing a bed of adsorbent (i.e., adsorbent bed).

An adsorbent bed is a bed of adsorbent contained within an adsorbent bed chamber. An adsorbent column includes multiple adsorbent beds. An adsorbent apparatus has one or more adsorbent columns. Any fluid in an adsorbent bed chamber, whether or not adsorbed on an adsorbent, is considered to be part of the bed. Accordingly, when fluid is introduced into or withdrawn from an adsorbent bed chamber, the fluid is considered as being introduced or withdrawn, into or from the bed itself.

An adsorbent is a solid material, which selectively adsorbs at least one $C_8$ aromatic in preference to other $C_8$ aromatics. In a simulated moving bed apparatus, such as a Parex™ unit, examples of adsorbents include charcoal, ion-exchange resins, silica gel, activated carbon, zeolitic material, and the like. An adsorbent, which is particularly useful for separating paraxylene from other $C_8$ aromatics, is a faujasite-type molecular sieve material, such as zeolite X or zeolite Y, optionally, substituted or treated with an enhancing agent, such as a Group I or II element, such as potassium or barium. Examples of adsorbents for separating paraxylene from other $C_8$ aromatics are described in U.S. Pat. No. 3,761,533.

An example of an adsorbent for separating ethylbenzene from metaxylene and orthoxylene is a titanosilicate adsorbent, as described in U.S. Pat. Nos. 6,369,287; 5,244,650; 5,001,591; and 4,853,202.

Adsorbent selectivity is the tendency of an adsorbent to adsorb a particular compound from a mixture of compounds. In a paraxylene separation process, the adsorbent will adsorb paraxylene at a faster rate than other $C_8$ aromatics. The adsorbent may also adsorb ethylbenzene at a faster rate than either metaxylene or orthoxylene.

A desorbent is a liquid which displaces $C_8$ aromatics from adsorbent. The desorbent may be equally or slightly more preferentially adsorbed on the adsorbent than paraxylene. The adsorbent may have a greater selectivity for the desorbent than other $C_8$ aromatics. The desorbent should have a boiling point significantly different than the boiling points of $C_8$ aromatics, such that the desorbent may be separated from $C_8$ aromatics by distillation. Examples of desorbents for a paraxylene separation process include paradiethylbenzene and toluene.

Unless otherwise specified herein, the terms, downstream and upstream, refer to the direction of flow of circulating bulk fluid.

A number of abbreviations are used herein. PX stands for paraxylene. MX stands for metaxylene. OX stands for orthoxylene. EB stands for ethylbenzene. pDEB stands for paradiethylbenzene. TOL stands for toluene. NA stands for non-aromatics such as paraffins, may be introduced into an adsorption apparatus as a feed impurity, especially when the feed comprises $C_8$ aromatics obtained from a reforming process. SMB stands for simulated moving bed.

FIG. 1

FIG. 1 illustrates a standard SMB apparatus with 24 adsorbent beds. This 24 bed configuration is particularly useful for separating one $C_8$ aromatic, such as PX, from a mixture of $C_8$ aromatics, such as a mixture of PX, MX, OX, and EB.

In FIG. 1, twelve adsorbent beds 101-112 are stacked in a first column 191 and another twelve adsorbent beds 113-124 are stacked in a second column 192. Conduits in fluid communication with a fluid distribution device are depicted by double arrows 131-154. The double arrows reflect the possibility of fluid flow either into or out of columns 191 and 192 during the multiple steps of the SMB process. For simplicity, the fluid distribution device is not shown in FIG. 1. Also, not shown in FIG. 1 are fluid collection areas between beds. However, it will be understood that such collection areas, such as those represented as downcomers as described in U.S. Pat. No. 3,201,491, may be present in columns 191 and 192 of FIG. 1.

Figure 2:
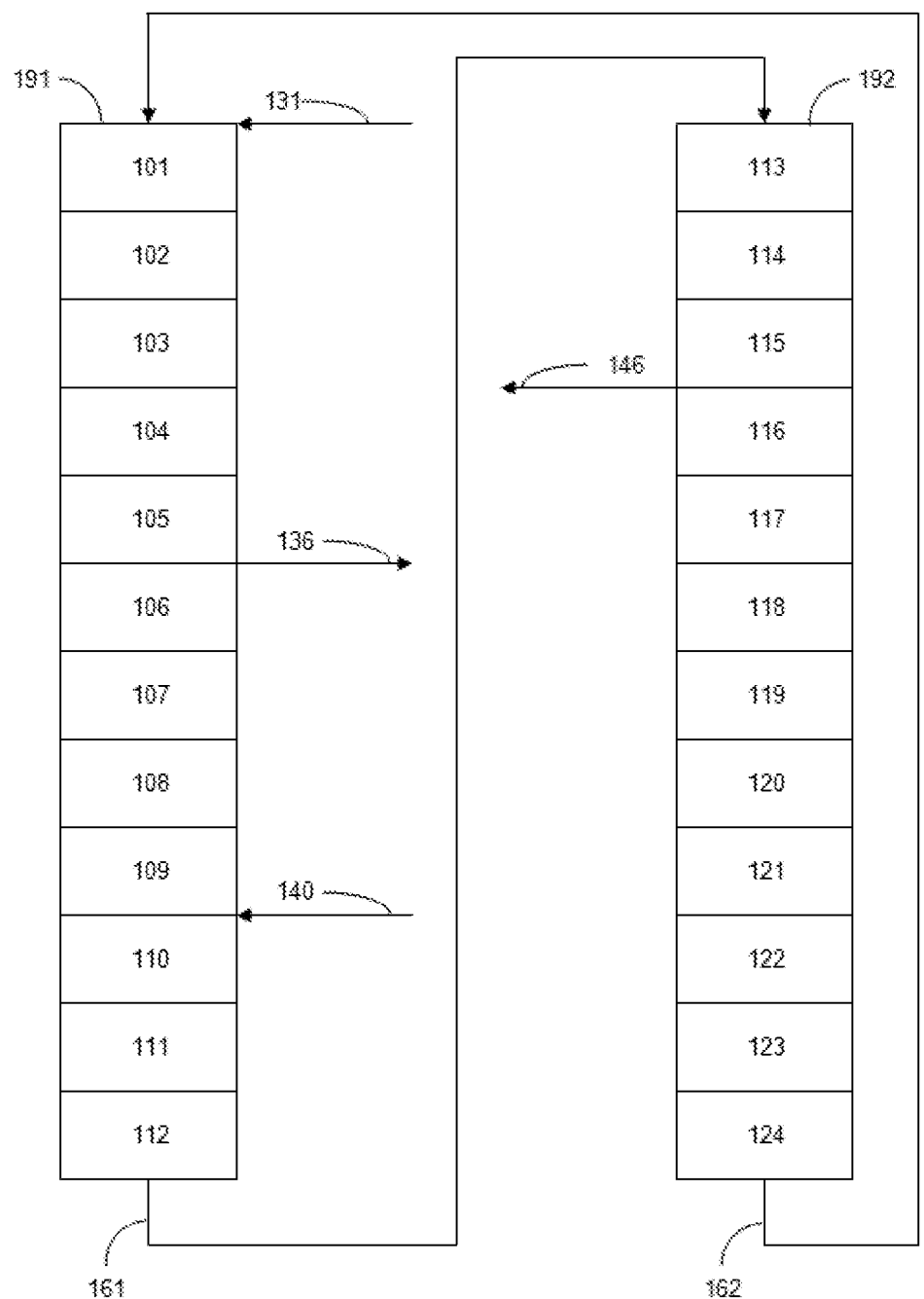
FIG. 2 is a schematic illustration showing the direction of flow of streams during a step of standard simulated moving bed adsorptive separation system.

A circulating bulk fluid, which is taken from the bottom of column 192 and bed 124, is introduced into the top of column 191 and bed 101 through line 162 shown in FIG. 2. The circulating bulk fluid flows in a downward direction through each of the beds of the first column 191 and is then transported to the top of the second column 192 through line 161. The circulating bulk fluid then flows in a downward direction through each of the beds of the second column 192.

FIG. 2

FIG. 2 shows the flow of fluids through columns 191 and 192 during a single step of an adsorption cycle. The flow of fluids in FIG. 2 represents a standard SMB operation, where a single separation takes place in an SMB unit with 24 beds. In particular, PX is separated from a mixture comprising PX, MX, OX, and EB.

Numbered features in FIG. 2 correspond to numbered features in FIG. 1. In FIG. 2, the double arrows in FIG. 1 are replaced with single arrows to show the actual direction of flow of fluids during a single step.

The following steps occur at the same time in columns 191 and 192. A feed, which comprises a mixture of PX, MX, OX, and EB, is introduced into the top of bed 101 in column 191 via conduit 131. A raffinate stream, which comprises a desorbent, MX, OX, and EB, is withdrawn from the top of bed 106 through conduit 136. A desorbent stream is introduced into the top of bed 110 through conduit 140. The desorbent may be, for example, pDEB, TOL, or tetralin. An extract stream, which comprises desorbent and PX, is withdrawn from the top of bed 116 through conduit 146.

At the end of the step shown in FIG. 2, i.e., after the step time, the fluid distribution device shifts the flow of streams one bed downstream from the beds shown in FIG. 2. In particular, referring to both FIGS. 1 and 2, the next step is performed by (1) directing the flow of the feed stream to the top of bed 102 via conduit 132, (2) directing the flow of the raffinate stream from the top of bed 107 via conduit 137, (3) directing the flow of the desorbent stream to the top of bed 111 via conduit 141, and (4) directing the flow of the extract stream from the top of bed 117 via conduit 147.

FIG. 3

Figure 3:
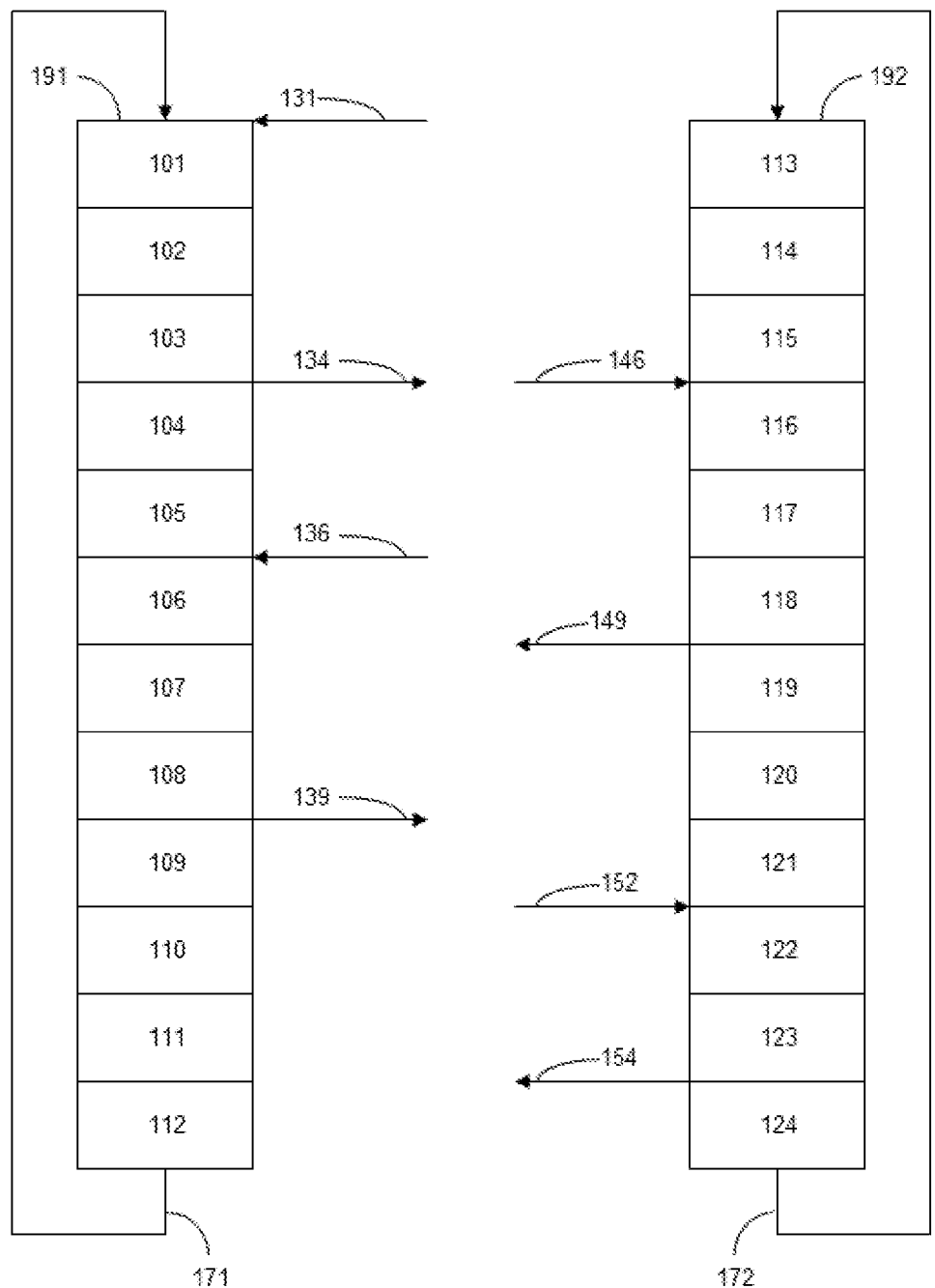
FIGS. 3-6 are schematic illustrations showing the direction of flow of streams during a step of simulated moving bed adsorptive separation system according to embodiments disclosed herein that use a PowerFeed process.

FIG. 3 shows one embodiment in which the two columns of a conventional commercial SMB apparatus are operated independently as two adsorption zones and each column performs a different separation. In reference to FIG. 3 only, column 191 is interchangeable with the first adsorption zone and column 192 is interchangeable with the second adsorption zone. There is no circulation between the two columns, but a circulating bulk fluid is maintained within column 191 and a circulating bulk fluid is maintained within column 192. A first separation takes place in column 191, operated as a separate and independent SMB unit with 12 beds, and a second separation takes place in column 192, operated as a separate and independent SMB unit with 12 beds. In a preferred embodiment, the raffinate stream from the first column is used as the feed stream to the second column.

FIG. 3 shows the flow of fluids through columns 191 and 192 during a single step of an adsorption cycle for each of the columns. The flow of fluids in FIG. 3 represents a modified SMB operation, where two separations take place. In particular, the flow of fluids in FIG. 3 is designed to achieve a dual separation, where PX is separated in column 191/first adsorption zone from a mixture comprising PX, MX, OX, and EB, and then the raffinate from column 191, comprising MX, OX, and EB, is provided to column 192/second adsorption zone to recover a $C_8$ aromatic other than PX or a non-aromatic $C_{8+}$ hydrocarbon.

Numbered features in FIG. 3 correspond to numbered features in FIG. 1. In FIG. 3, the double arrows in FIG. 1 are replaced with single arrows to show the actual direction of flow of fluids during a single step. Also, in FIG. 3, a flow of circulating bulk fluid is maintained in column 191 and a flow of circulating bulk fluid is maintained in column 192, but there is no circulation of bulk fluid between the columns. This separate flow is achieved by replacing conduits 161 and 162 in FIG. 1 with conduits 171 and 172 in FIG. 3. Conduit 171 directs flow of fluid from the bottom of bed 112 to the top of bed 101 in column 191, and conduit 172 directs flow of fluid from the bottom of bed 124 to the top of bed 113 in column 192.

The following steps occur at the same time. A first feed, which comprises a mixture of PX, MX, OX, and EB, is introduced into the top of bed 101 in column 191 via conduit 131. A first raffinate stream, which comprises a desorbent, MX, OX, and EB, is withdrawn from the top of bed 104 through conduit 134. A first desorbent stream is introduced into the top of bed 106 through conduit 136. The desorbent may be, for example, pDEB, TOL, or tetralin. A first extract stream, which comprises desorbent and PX, is withdrawn from the top of bed 109 through conduit 139.

The first raffinate from the first column 191 is directed as a second feed to the top of bed 116 in column 192 via conduit 146. Desorbent in first raffinate may be removed, e.g., by distillation, prior to the introduction of the feed to the top of bed 116 of column 192 via conduit 146. A second raffinate stream is withdrawn from the top of bed 119 through conduit 149, a second desorbent stream is introduced into the top of bed 122 through conduit 152, and a second extract stream is withdrawn from the top of bed 124 through conduit 154.

The composition of the second raffinate and the second extract depends on the nature of the adsorbent in beds 113-124 of column 192. If the adsorbent is selective for EB, then the second raffinate will comprise MX and OX, and the second extract will comprise EB. If the adsorbent is selective for MX, then the second raffinate will may comprise OX and EB, and the second extract will comprise MX. If the adsorbent is selective for OX, then the second raffinate will comprise MX and EB, and the second extract will comprise OX. If the second feed comprises a non-aromatic hydrocarbon, such as a non-aromatic hydrocarbon having 8 or more carbon atoms that was not removed prior to the PX separation (due to similar boiling points or other reasons), and if the adsorbent is selective for the non-aromatic hydrocarbon, then the second raffinate will comprise MX, OX, and EB, and the second extract will comprise the non-aromatic $C_{8+}$ hydrocarbon.

The adsorbent used in the beds of columns 191 and 192 may be the same or different. In one embodiment, a primarily PX-selective adsorbent such as zeolite X exchanged with barium is used in both columns. In another embodiment, a PX-selective adsorbent such as zeolite X exchanged with barium is used in the first column (first adsorption zone) and an EB-selective adsorbent such as a titanosilicate or an OX-selective adsorbent such as MIL-47(V) is used in the second column (second adsorption zone). The desorbent used in columns 191 and 192 may be the same or different. The step time intervals of the separations taking place in columns 191 and 192 may be the same or different. In one embodiment, the step time in columns 191 and 192 is interval X. In another embodiment, the step time in column 191 is interval X and the step time in column 192 is interval Y, which is different than interval X.

A PowerFeed process is preferably used in column 191, and a PowerFeed process may or may not be used in column 192. Thus, in column 191/first adsorption zone, the flow rate of at least one stream is varied during step time interval X. In order to maintain mass balance within the first adsorption zone, the flow rate of at least one other stream is adjusted proportionally. For example, if the flow rate of the feed stream is increased during time interval X, the flow rate of the desorbent stream should be decreased, and/or the flow rate of at least one of the extract stream and/or the raffinate should be increased to compensate for the increased rate of flow of fluid introduced into the first adsorption zone.

At the end of the step conducted in column 191 shown in FIG. 3, i.e., after the step time, the fluid distribution device shifts the flow of streams one bed downstream from the beds shown in FIG. 3. In particular, referring to both FIGS. 1 and 3, the next step is performed by (1) directing the flow of the first feed stream to the top of bed 102 via conduit 132, (2) directing the flow of the first raffinate stream from the top of bed 105 via conduit 135, (3) directing the flow of the first desorbent stream to the top of bed 107 via conduit 137, and (4) directing the flow of the first extract stream from the top of bed 110 via conduit 140.

At the end of the step conducted in column 192 shown in FIG. 3, the fluid distribution device shifts the flow of streams one bed downstream from the beds shown in FIG. 3. In particular, referring to both FIGS. 1 and 3, the next step is performed by (1) directing the flow of the second feed stream to the top of bed 117 via conduit 147, (2) directing the flow of the second raffinate stream from the top of bed 120 via conduit 150, (3) directing the flow of the second desorbent stream to the top of bed 123 via conduit 153, and (4) directing the flow of the second extract stream from the top of bed 113 via conduit 143.

FIG. 4

Figure 4:
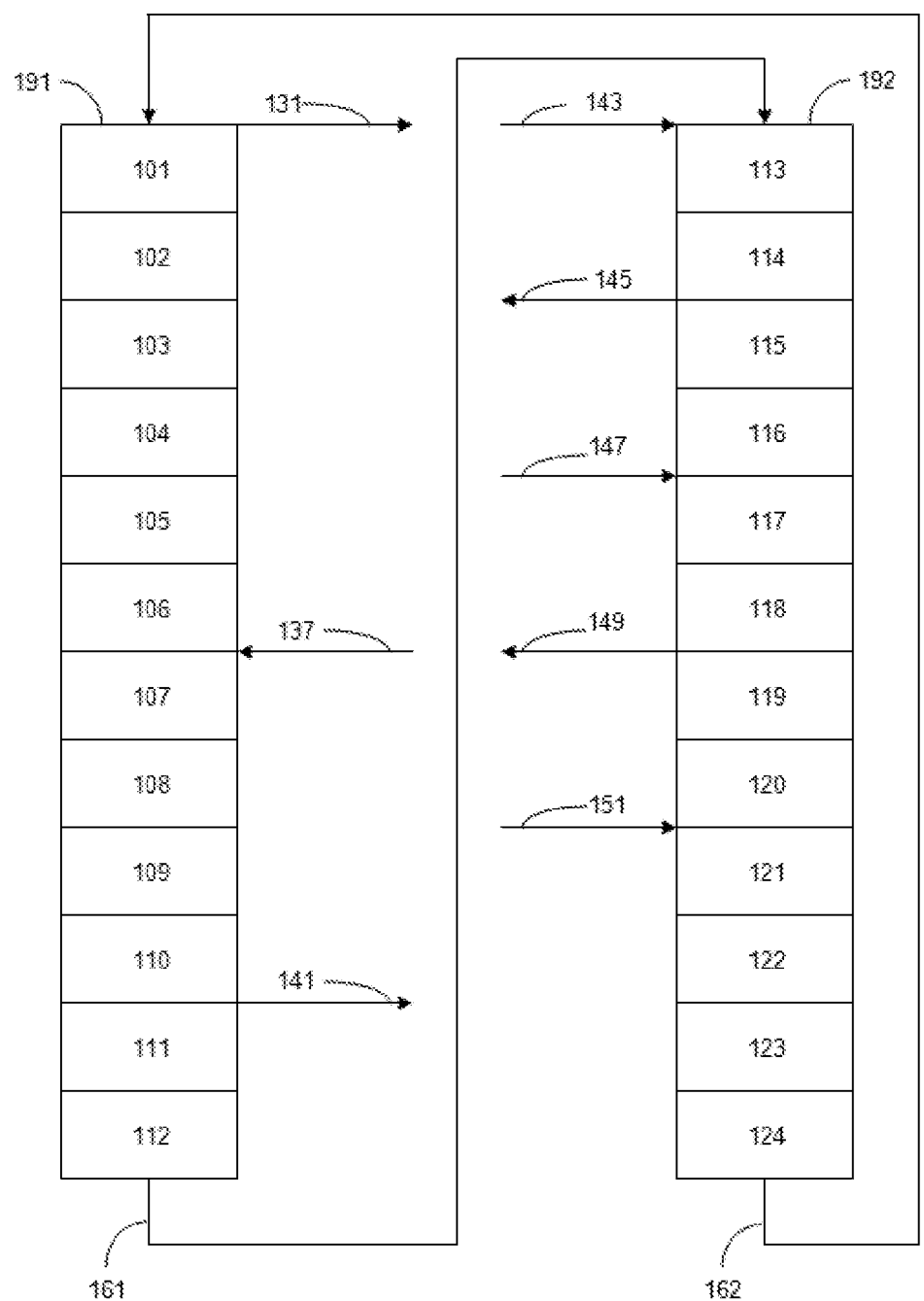

FIG. 4 shows an embodiment in which two separations are conducted in a conventional commercial SMB apparatus having 24 beds. A first separation takes place in a first adsorption zone of the unit having 16 beds, and a second separation takes place in a second adsorption zone of the unit having 8 beds. In a preferred embodiment, the raffinate stream from the first adsorption zone is used as the feed stream to the second adsorption zone.

FIG. 4 shows the flow of fluids through columns 191 and 192 during a single step of an adsorption cycle. The flow of fluids in FIG. 4 represents a modified SMB operation, where two separations take place in an SMB unit with 24 beds. In particular, the flow of fluids in FIG. 4 is designed to achieve a dual separation, where PX is separated from a mixture comprising PX, MX, OX, and EB to produce a raffinate, and then a $C_8$ aromatic other than PX or a non-aromatic $C_{8+}$ hydrocarbon is separated from the raffinate.

Numbered features in FIG. 4 correspond to numbered features in FIG. 1. In FIG. 4, the double arrows in FIG. 1 are replaced with single arrows to show the actual direction of flow of fluids during a single step.

The following steps occur at the same time in columns 191 and 192. A first feed, which comprises a mixture of PX, MX, OX, and EB, is introduced into the top of bed 107 via conduit 137. A first raffinate stream, which comprises a desorbent, MX, OX, and EB, is withdrawn from the top of bed 111 through conduit 141. A first desorbent stream is introduced into the top of bed 121 through conduit 151. The first desorbent may be pDEB, TOL, or tetralin. A first extract stream, which comprises desorbent and PX, is withdrawn from the top of bed 101 through conduit 131.

The first raffinate in conduit 141 is directed as a second feed to the top of bed 117 of column 192 via conduit 147. Desorbent in first raffinate may be removed, e.g., by distillation, prior to the introduction of the feed to the top of bed 117. A second raffinate stream is withdrawn from the top of bed 119 through conduit 149, a second desorbent stream is introduced into the top of bed 113 through conduit 143, and a second extract stream is withdrawn from the top of bed 115 through conduit 145.

The adsorbent used in the beds of columns 191 and 192 of FIG. 4 has a primary selectivity for PX and a secondary selectivity for at least one of MX, OX, and EB. The composition of the second raffinate and the second extract depends on the secondary selectivity of the adsorbent. If the adsorbent is more selective for EB than MX and OX, then the second raffinate will comprise MX and OX, and the second extract will comprise EB. If the adsorbent is more selective for MX than EB and OX, then the second raffinate will comprise OX and EB, and the second extract will comprise MX. If the adsorbent is more selective for OX than MX and EB, then the second raffinate will comprise MX and EB, and the second extract will comprise OX.

A PowerFeed process is used to achieve the first separation in the first adsorption zone of the SMB unit containing 16 beds, represented by beds 101-112 and beds 121-124 of FIG. 4. Thus, in the first adsorption zone, the flow rate of at least one stream is varied during step time interval X. In order to maintain mass balance within the first adsorption zone, the flow rate of at least one other stream is adjusted proportionally. For example, if the flow rate of the feed stream is increased during time interval X, the flow rate of the desorbent stream should be decreased, and/or the flow rate of at least one of the extract stream and/or the raffinate should be increased to compensate for the increased rate of flow of fluid introduced into the first adsorption zone.

A PowerFeed process may or may not be used to achieve the second separation in the second adsorption zone of the SMB unit containing 8 beds, represented by beds 113-120 of FIG. 4.

At the end of a step conducted in columns 191 and 192 shown in FIG. 4, the fluid distribution device shifts the flow of streams one bed downstream from the beds shown in FIG. 4. In particular, referring to both FIGS. 1 and 4, the next step is performed by (1) directing the flow of the first feed stream to the top of bed 108 via conduit 138, (2) directing the flow of the first raffinate stream from the top of bed 112 via conduit 142, (3) directing the flow of the first desorbent stream to the top of bed 122 via conduit 152, (4) directing the flow of the first extract stream from the top of bed 102 via conduit 132, (5) directing the flow of the second feed stream to the top of bed 118 via conduit 148, (6) directing the flow of the second raffinate stream from the top of bed 120 via conduit 150, (7) directing the flow of the second desorbent stream to the top of bed 114 via conduit 144, and (8) directing the flow of the second extract stream from the top of bed 116 via conduit 146. In the embodiment shown in FIG. 4, the first and second adsorption zones each shift one bed downstream after each step.

During operation, the beds of the two adsorption zones of the SMB apparatus shown in FIGS. 2-4 may be considered to be divided into four sub-zones. These sub-zones are (1) the adsorption sub-zone, (2) the purification sub-zone, (3) the desorption sub-zone, and (4) the buffer sub-zone. The purification zone has also been referred to being the rectification zone. These sub-zones are described in the art, for example, in U.S. Pat. No. 8,569,564. In the FIG. 4 embodiment, the first adsorption sub-zone includes the beds between the first feed introduction point and the first raffinate withdrawal point, i.e., beds 107-110, the first purification sub-zone includes the beds between the first extract withdrawal point and the first feed introduction point, i.e., beds 101-106, the first desorption sub-zone includes the beds between the first desorbent introduction point and the first extract withdrawal point, i.e., beds 121-124, and the first buffer sub-zone includes the beds between the first raffinate withdrawal point and the first desorbent introduction point, i.e., beds 111-120. The second adsorption sub-zone includes the beds between the second feed introduction point and the second raffinate withdrawal point, i.e., beds 117-118, the second purification sub-zone includes the beds between the second extract withdrawal point and the second feed introduction point, i.e., beds 115-116, the second desorption sub-zone includes the beds between the second desorbent introduction point and the second extract withdrawal point, i.e., beds 113-114, and the second buffer sub-zone includes the beds between the second raffinate withdrawal point and the second desorbent introduction point, i.e., beds 119-120.

In the configuration of beds shown in FIG. 4, the first simulated moving-bed adsorption zone and the second adsorption zone are connected in series. The second adsorption zone is preferably located within the first adsorption zone in a position to minimize the effects of contamination from the circulating flow of fluids within the two zones. As shown in FIG. 4, the second adsorption zone is included in the buffer zone of the first adsorption zone, i.e., the first buffer sub-zone, because this section of the first adsorption zone has the lowest concentration of $C_8$ aromatic compounds.

FIG. 5

Figure 5:
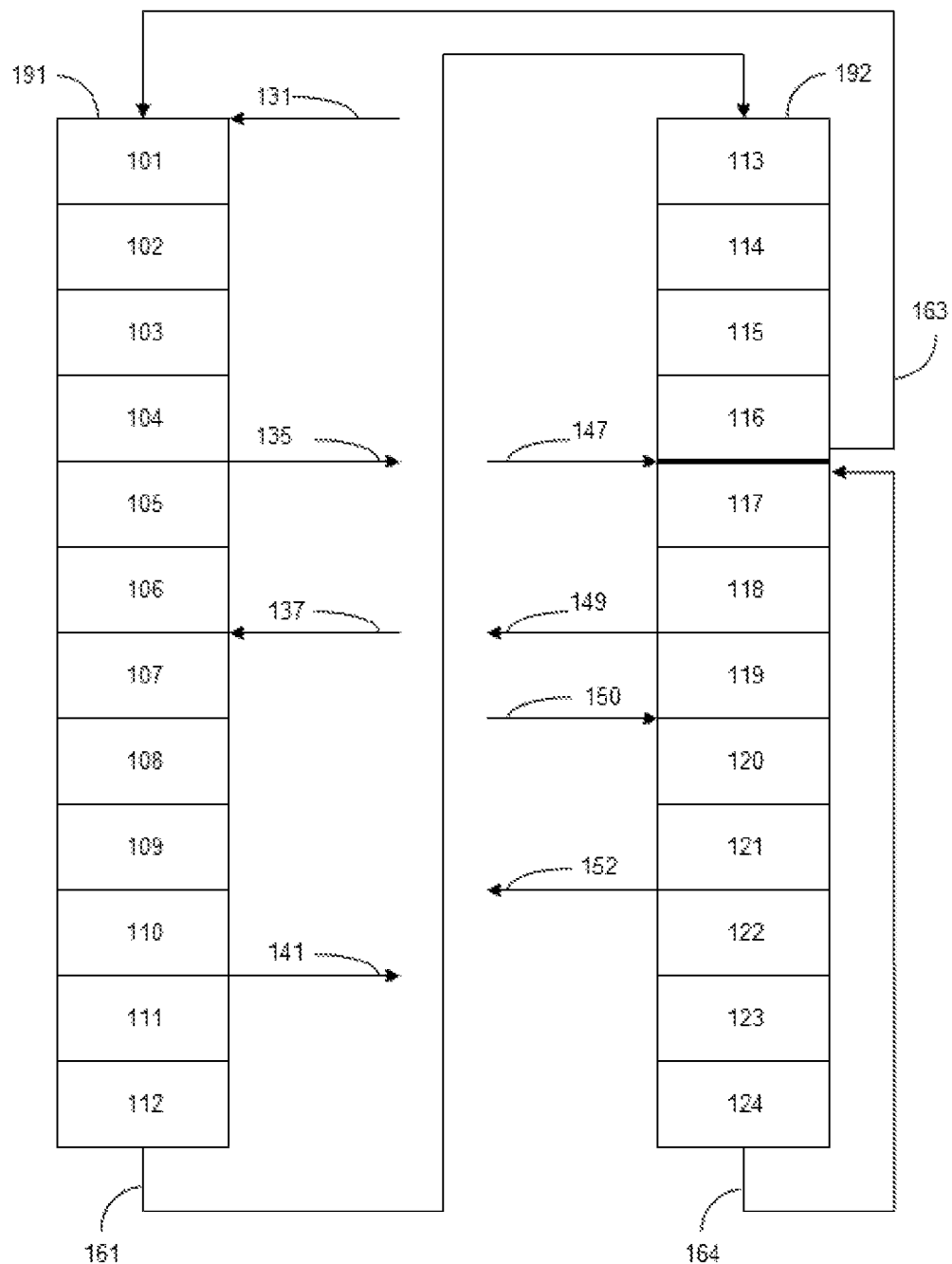

FIG. 5 shows another embodiment in which two separations are conducted in a conventional commercial SMB apparatus having 24 beds. A first separation takes place in a first adsorption zone of the unit having 16 beds, and a second separation takes place in a second adsorption zone of the unit having 8 beds. In a preferred embodiment, the raffinate stream from the first adsorption zone is used as the feed stream to the second segment. In contrast to the embodiment shown in FIG. 4, there is no circulation of bulk fluid between the two adsorption zones in this embodiment. A barrier may be placed between the zones to prevent fluid from the first adsorption zone from flowing into the second adsorption zone.

FIG. 5 shows the flow of fluids through columns 191 and 192 during a single step of an adsorption cycle. The flow of fluids in FIG. 5 represents a modified SMB operation, where two separations take place in a SMB unit with 24 beds. In particular, the flow of fluids in FIG. 5 is designed to achieve a dual separation, where PX is separated from a mixture comprising PX, MX, OX, and EB in the first adsorption zone containing 16 beds, represented by beds 101-116 in FIG. 5, to produce a raffinate, and then a $C_8$ aromatic other than PX or a non-aromatic $C_{8+}$ hydrocarbon is separated from the raffinate in the second adsorption zone containing 8 beds, represented by beds 117-124 in FIG. 5.

Numbered features in FIG. 5 correspond to numbered features in FIG. 1. In FIG. 5, the double arrows in FIG. 1 are replaced with single arrows to show the actual direction of flow of fluids during a single step. Also, in FIG. 5, a flow of circulating bulk fluid is maintained in the first adsorption zone and a flow of circulating bulk fluid is maintained in the second adsorption zone, but there is no circulation between the zones. This separate flow is achieved by replacing conduit 162 in FIG. 1 with conduits 163 and 164 in FIG. 5 and placing a barrier between beds 116 and 117. For the first adsorption zone, conduit 161 directs flow of fluid from the bottom of bed 112 to the top of bed 113 in column 192, and conduit 163 directs flow of fluid from the bottom of bed 116 to the top of bed 101 in column 191. For the second adsorption zone, conduit 164 directs flow of fluid from the bottom of bed 124 to the top of bed 117 in column 192.

The following steps occur at the same time in columns 191 and 192. A first feed, which comprises a mixture of PX, MX, OX, and EB, is introduced into the top of bed 101 via conduit 131. A first raffinate stream, which comprises a desorbent, MX, OX, and EB, is withdrawn from the top of bed 105 through conduit 135. A first desorbent stream is introduced into the top of bed 107 through conduit 137. The first desorbent may be pDEB, TOL, or tetralin. A first extract stream, which comprises desorbent and PX, is withdrawn from the top of bed 111 through conduit 141.

The first raffinate in conduit 135 is directed as a second feed to the top of bed 117 of column 192 via conduit 147. Desorbent in first raffinate may be removed, e.g., by distillation, prior to the introduction of the feed to the top of bed 117. A second raffinate stream is withdrawn from the top of bed 119 through conduit 149, a second desorbent stream is introduced into the top of bed 120 through conduit 150, and a second extract stream is withdrawn from the top of bed 122 through conduit 152.

The adsorbent used in the beds of the first and second adsorption zones may be the same or different. In one embodiment, a primarily PX-selective adsorbent such as zeolite X exchanged with barium is used in both zones. In another embodiment, a PX-selective adsorbent such as zeolite X exchanged with barium is used in the first adsorption zone and an EB-selective adsorbent such as a titanosilicate or an OX-selective adsorbent such as MIL-47(V) is used in the second adsorption zone. The desorbent used in the first and second adsorption zones may be the same or different. The step time intervals of the separations taking place in the first and second adsorption zones may be the same or different.

A PowerFeed process is preferably used in the first adsorption zone, and a PowerFeed process may or may not be used in the second adsorption zone. Thus, in the first adsorption zone, the flow rate of at least one stream is varied during step time interval X. In order to maintain mass balance within the first adsorption zone, the flow rate of at least one other stream is adjusted proportionally. For example, if the flow rate of the feed stream is increased during time interval X, the flow rate of the desorbent stream should be decreased, and/or the flow rate of at least one of the extract stream and/or the raffinate should be increased to compensate for the increased rate of flow of fluid introduced into the first adsorption zone.

At the end of a step conducted in the first and second adsorption zones shown in FIG. 5, the fluid distribution device shifts the flow of streams one bed downstream from the beds shown in FIG. 5. In particular, referring to both FIGS. 1 and 5, the next step is performed by (1) directing the flow of the first feed stream to the top of bed 102 via conduit 132, (2) directing the flow of the first raffinate stream from the top of bed 106 via conduit 136, (3) directing the flow of the first desorbent stream to the top of bed 108 via conduit 138, (4) directing the flow of the first extract stream from the top of bed 112 via conduit 142, (5) directing the flow of the second feed stream to the top of bed 118 via conduit 148, (6) directing the flow of the second raffinate stream from the top of bed 120 via conduit 150, (7) directing the flow of the second desorbent stream to the top of bed 121 via conduit 151, and (8) directing the flow of the second extract stream from the top of bed 123 via conduit 153. In the embodiment shown in FIG. 5, the first and second adsorption zones each shift one bed downstream after each step.

FIG. 6

Figure 6:
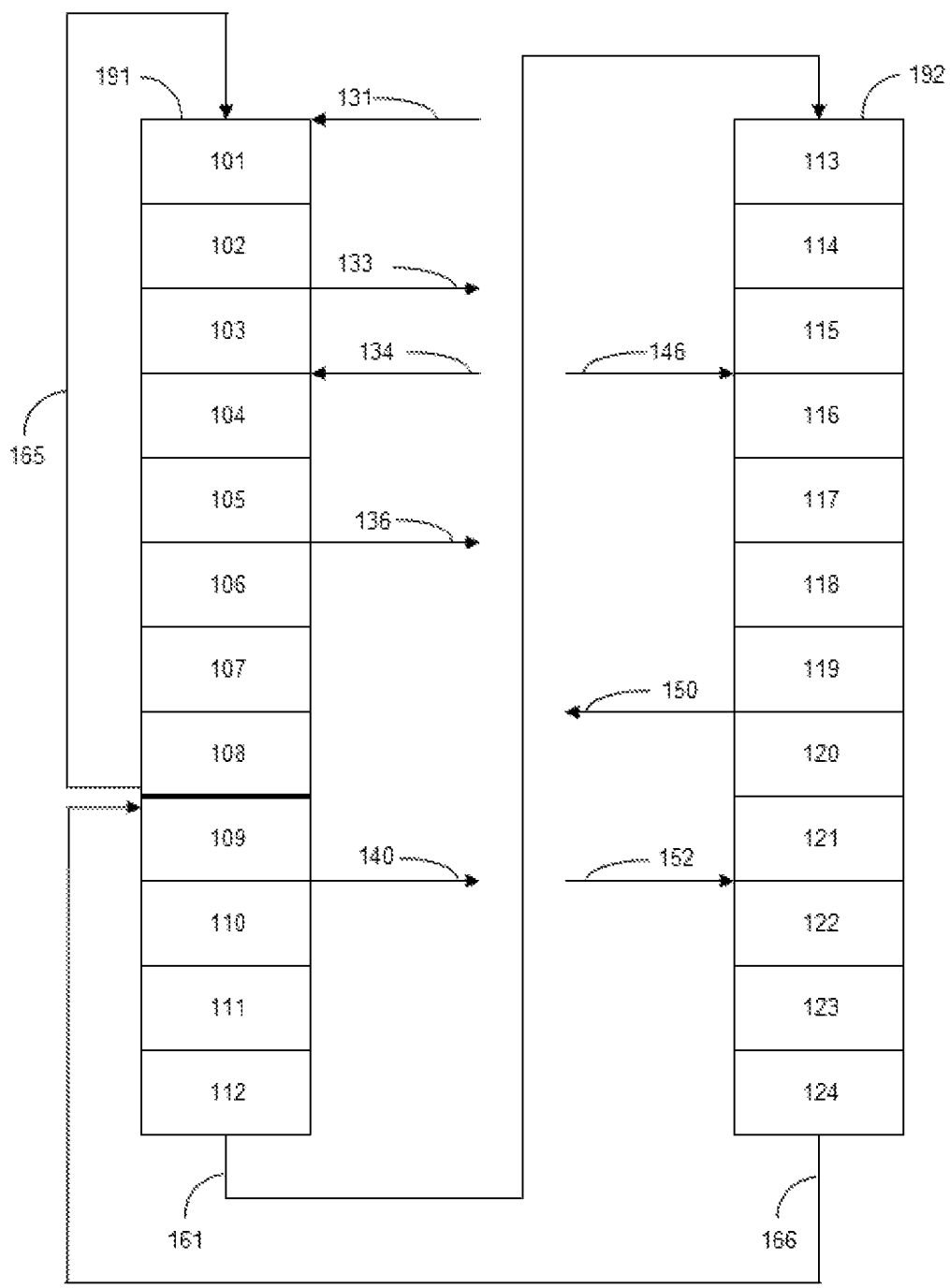

FIG. 6 shows another embodiment in which two separations are conducted in a conventional commercial SMB apparatus having 24 beds. A first separation takes place in a first adsorption zone of the unit having 8 beds, and a second separation takes place in a second adsorption zone of the unit having 16 beds. In a preferred embodiment, the raffinate stream from the first adsorption zone is used as the feed stream to the second segment. In contrast to the embodiment shown in FIG. 4, and like the embodiment shown in FIG. 5, there is no circulation of bulk fluid between the two adsorption zones in this embodiment. A barrier may be placed between the zones to prevent fluid from the first adsorption zone from flowing into the second adsorption zone.

FIG. 6 shows the flow of fluids through columns 191 and 192 during a single step of an adsorption cycle. The flow of fluids in FIG. 6 represents a modified SMB operation, where two separations take place in a SMB unit with 24 beds. In particular, the flow of fluids in FIG. 6 is designed to achieve a dual separation, where PX is separated from a mixture comprising PX, MX, OX, and EB in the first adsorption zone containing 8 beds, represented by beds 101-108 in FIG. 6, to produce a raffinate, and then a $C_8$ aromatic other than PX or a non-aromatic $C_{8+}$ hydrocarbon is separated from the raffinate in the second adsorption zone containing 16 beds, represented by beds 109-124 in FIG. 6.

Numbered features in FIG. 6 correspond to numbered features in FIG. 1. In FIG. 6, the double arrows in FIG. 1 are replaced with single arrows to show the actual direction of flow of fluids during a single step. Also, in FIG. 6, a flow of circulating bulk fluid is maintained in the first adsorption zone and a flow of circulating bulk fluid is maintained in the second adsorption zone. In one embodiment, there is fluid communication between the zones, but in another embodiment, there is no circulation between the zones. This separate flow is achieved by replacing conduit 162 in FIG. 1 with conduits 165 and 165 in FIG. 6 and placing a barrier between beds 108 and 109. For the first adsorption zone, conduit 165 directs flow of fluid from the bottom of bed 108 to the top of bed 101 in column 191. For the second adsorption zone, conduit 161 directs flow of fluid from the bottom of bed 112 to the top of bed 113 in column 192, and conduit 166 directs flow of fluid from the bottom of bed 124 to the top of bed 109 in column 191.

The following steps occur at the same time in columns 191 and 192. A first feed, which comprises a mixture of PX, MX, OX, and EB, is introduced into the top of bed 101 via conduit 131. A first raffinate stream, which comprises a desorbent, MX, OX, and EB, is withdrawn from the top of bed 103 through conduit 133. A first desorbent stream is introduced into the top of bed 104 through conduit 134. The first desorbent may be pDEB, TOL, or tetralin. A first extract stream, which comprises desorbent and PX, is withdrawn from the top of bed 106 through conduit 136.

The first raffinate in conduit 133 is directed as a second feed to the top of bed 116 of column 192 via conduit 146. Desorbent in first raffinate may be removed, e.g., by distillation, prior to the introduction of the feed to the top of bed 116. A second raffinate stream is withdrawn from the top of bed 120 through conduit 150, a second desorbent stream is introduced into the top of bed 122 through conduit 152, and a second extract stream is withdrawn from the top of bed 110 through conduit 140.

The adsorbent used in the beds of the first and second adsorption zones may be the same or different. In one embodiment, a primarily PX-selective adsorbent such as zeolite X exchanged with barium is used in both zones. In another embodiment, a PX-selective adsorbent such as zeolite X exchanged with barium is used in the first adsorption zone and an EB-selective adsorbent such as a titanosilicate or an OX-selective adsorbent such as MIL-47(V) is used in the second adsorption zone. The desorbent used in the first and second adsorption zones may be the same or different. The step time intervals of the separations taking place in the first and second adsorption zones may be the same or different.

A PowerFeed process is preferably used in the first adsorption zone, and a PowerFeed process may or may not be used in the second adsorption zone. Thus, in the first adsorption zone, the flow rate of at least one stream is varied during step time interval X. In order to maintain mass balance within the first adsorption zone, the flow rate of at least one other stream is adjusted proportionally. For example, if the flow rate of the feed stream is increased during time interval X, the flow rate of the desorbent stream should be decreased, and/or the flow rate of at least one of the extract stream and/or the raffinate should be increased to compensate for the increased rate of flow of fluid introduced into the first adsorption zone.

At the end of a step conducted in the first and second adsorption zones shown in FIG. 6, the fluid distribution device shifts the flow of streams one bed downstream from the beds shown in FIG. 6. In particular, referring to both FIGS. 1 and 5, the next step is performed by (1) directing the flow of the first feed stream to the top of bed 102 via conduit 132, (2) directing the flow of the first raffinate stream from the top of bed 104 via conduit 134, (3) directing the flow of the first desorbent stream to the top of bed 105 via conduit 135, (4) directing the flow of the first extract stream from the top of bed 107 via conduit 137, (5) directing the flow of the second feed stream to the top of bed 117 via conduit 147, (6) directing the flow of the second raffinate stream from the top of bed 121 via conduit 151, (7) directing the flow of the second desorbent stream to the top of bed 123 via conduit 153, and (8) directing the flow of the second extract stream from the top of bed 111 via conduit 141. In the embodiment shown in FIG. 6, the first and second adsorption zones each shift one bed downstream after each step.

The Feed

The first feed may comprise a $C_8$ aromatic mixture of PX, OX, MX, and EB. This $C_8$ aromatic mixture may comprise equilibrium xylenes with a concentration of PX from 15 to 30 volume percent, for example, from 15 to 27 volume percent, for example, from 21 to 24 volume percent. The first feed may also comprise enhanced PX having a concentration of from 70 to 85 volume percent, for example, from 70 to 80 volume percent, PX.

According to one embodiment, at least 50 volume percent of the $C_8$ aromatic mixture may be produced by at least one refinery or petrochemical process. Examples of refinery or petrochemical processes for producing equilibrium xylenes include a reforming process, an isomerization process, a transalkylation process, and a mixture of any of these processes. An example of a refinery or petrochemical process for producing enhanced PX, which comprises from 75 to 98 volume percent of PX, is a selective TOL disproportionation process, a selective benzene or TOL methylation process, or a selective process for converting methanol to PX.

The feed may optionally comprise a small amount, for example, at least 1 wt %, of at least one non-aromatic compound, such as n-nonane. When the feed comprises such a non-aromatic compound, the non-aromatic compound may be separated from $C_8$ aromatics in the second adsorption zone.

Adsorbents and Desorbents

When PX is separated from a mixture of $C_8$ aromatics, the adsorbent may be, for example, one of those that are described in U.S. Pat. Nos. 3,626,020 and. 3,878,127. Such an adsorbent may be an X zeolite that is exchanged with barium and hydrated or a Y zeolite that is exchanged with potassium and barium. The desorbent for this PX separation process may comprise pDEB, TOL, or tetralin. A tetralin desorbent is described in U.S. Pat. No. 8,283,274.

When EB is separated from a mixture of $C_8$ aromatics, e.g., from which PX has been separated, the adsorbent may be the same as or different from the adsorbent used to separate PX from a mixture of $C_8$ aromatics. Such an adsorbent may contain at least one element that is selected from the group of elements K, Rb, Cs, Ba, Ca, and Sr and optionally water. Examples of such EB selective adsorbents are described in, for example, U.S. Pat. Nos. 5,453,560; 4,613,725; 4,108,915; 4,079,094; and 3,943,182. Another type of an adsorbent for separating EB from a mixture of $C_8$ aromatics may comprise a titanosilicate. Titanosilicate-containing adsorbents may have a pore opening on the order of 8 Å. Such titanosilicate-containing adsorbents are described in U.S. Pat. Nos. 5,244,650; 5,011,591; and 4,853,202. When a titanosilicate-containing adsorbent is used to separate EB from a mixture of $C_8$ aromatics, the desorbent may be pDEB, TOL, or a mixture of thereof.

When MX or OX is separated from a mixture of $C_8$ aromatics, an adsorbent selective for either MX or OX may be used, such as a Metal Organic Frameworks (MOF). MOFs have metal ions or clusters of metal ions and organic molecules called linkers. Metal organic framework materials are described in U.S. Pat. Nos. 5,648,508 and 7,662,746, and U.S. Patent Publication No. 2009/0305040. The MOF adsorbent may be used in a SMB unit, and para-diethylbenzene, TOL, or 1,4-di-n-isopropylbenzene may be used as a desorbent.

Suitable MOF adsorbents for separating OX or MX from mixtures of C8 aromatics may be determined by testing MOFs on their ability to sorb OX or MX and the ability of desorbents to desorb the OX or MX. Examples of suitable OX selective MOFs are Cr-MIL-101, which is described in U.S. Pat. No. 8,704,031, and MIL-47 (V), which is described in Angew. Chem. Int. Ed. 2002; Phys. Chem. Phys., 2008, 10, 2979 and U.S. Pat. No. 9,102,609. When MIL-47 (V) is used as an OX selective adsorbent, the desorbent may be n-heptane.

When PX is separated from a mixture of $C_8$ aromatics, the extract stream withdrawn may comprise at least 99.7 volume percent of PX, based on the total volume of xylenes and EB present in the extract stream. The extract stream may be separated by distillation downstream to provide a purified PX product and a stream rich in desorbent, which may be recycled to for re-use in the SMB adsorptive separation process.

PowerFeed Operation

In the PowerFeed process, the flow rate of at least one stream into or out of the SMB adsorption apparatus or SMB adsorptive zone may be varied at least once during the step time of interval X. At the beginning of time interval X, the flow rates into and out of the SMB adsorption apparatus or SMB adsorptive zone may be held constant for a portion or subinterval of interval X. After the expiration of a first portion of X, the flow rates of at least one of the streams may be changed. Time interval X may be split into at least two portions or subintervals. The durations of each of the subintervals may be the same or different. For example, according to one embodiment described in Examples herein, time interval X is split up into four different portions of unequal duration.

In embodiments in which a different step time, time interval Y, is used in the second adsorption zone, and the PowerFeed process is also used, the the flow rate of at least one stream into or out of the second SMB adsorption apparatus zone may be varied at least once during time interval Y as described above in relation to time interval X. The following description is equally applicable to step time intervals different from time interval X, such as time interval Y or any other step time interval.

Especially when a single raffinate stream is withdrawn from a SMB adsorptive separation apparatus or SMB adsorptive zone, more of the $C_8$ aromatic feed may be introduced into the SMB adsorptive separation apparatus during the latter portion of time interval X than in the earlier portion of time interval X. For example, if X is 60 seconds, the flow of feed to a bed of the SMB adsorptive separation apparatus is switched every 60 seconds. When more of the feed is introduced into the SMB adsorptive separation apparatus during the latter portion of time interval X than in the earlier portion of time interval X, and X is 60 seconds, less of the total feed introduced during the 60 seconds would be introduced during the first 30 seconds of X, and more of the total feed introduced during the 60 seconds would be introduced during the last 30 seconds of X.

In a particular embodiment, less than 30% of the feed may be introduced into the SMB adsorptive separation apparatus or SMB adsorptive zone during a time subinterval of from 0 to 40% of X (i.e., a time interval extending over the first 40% of X), and at least 70% of the at least one multicomponent feed may be introduced into the SMB adsorptive separation apparatus during a time subinterval of from 40 to 100% of X (i.e., a time interval extending from the first 40% of X to the end of X). According to this embodiment, if X is 60 seconds, less than 30% of the at least one multicomponent feed would be introduced into the SMB adsorptive separation apparatus during the first 20 seconds of X, and at least 70% of the at least one multicomponent feed may be introduced into the SMB separation apparatus during the last 40 seconds of X.

In another embodiment, the flow of feed may be described in terms of five (5) subintervals of X. In particular, (1) less than 10% of the feed, which is introduced in time interval X, may be introduced during a time subinterval of from 0 to 20% of X (i.e., a time interval extending over the first 20% of X), (2) less than 15% of the feed, which is introduced in time interval X, may be introduced during a time subinterval of from 20 to 40% of X (i.e., a time interval extending from the end of the first 20% of X to the end of the first 40% of X), (3) at least 15% of the feed, which is introduced in time interval X, may be introduced during a time subinterval of from 40 to 60% of X (i.e., a time interval extending from the end of the first 40% of X to the end of the first 60% of X), (4) at least 20% of the feed, which is introduced in time interval X, may be introduced during a time subinterval of from 60 to 80% of X (i.e., a time interval extending from the end of the first 60% of X to the end of the first 80% of X), and (5) at least 20% of the feed, which is introduced in time interval X, may be introduced during a time subinterval of from 80 to 100% of X (i.e., a time interval extending from the end of the first 80% of X to the end of X). According to this embodiment, if X is 60 seconds, (1) less than 10% of the feed, which is introduced in time interval X, would be introduced during the first 12 seconds of X; (2) less than 15% of the feed, which is introduced in time interval X, would be introduced during a time subinterval of from 12 to 24 seconds from the start of X; (3) at least 15% of the feed, which is introduced in time interval X, would be introduced during a time subinterval of from 24 to 36 seconds from the start of X, (4) at least 20% of the feed, which is introduced in time interval X, would be introduced during a time subinterval of from 36 to 48 seconds from the start of X, and (5) at least 20% of the feed, which is introduced in time interval X, would be introduced during a time subinterval of from 48 to 60 seconds from the start of X. After 60 seconds the flow of feed to a bed would be interrupted and resumed in the next bed downstream in terms of the flow of circulating fluid in the SMB adsorptive separation apparatus.

The flow rate of other streams may also be varied during time interval X. For example, less of the raffinate stream may be withdrawn from the SMB adsorptive separation apparatus or SMB adsorptive zone during the latter portion of time interval X than in the earlier portion of time interval X. For example, if X is 60 seconds, the flow of raffinate from a bed of the SMB separation apparatus is switched every 60 seconds. When less of the raffinate is withdrawn from the SMB adsorptive separation apparatus during the latter portion of time interval X than in the earlier portion of time interval X, and X is 60 seconds, less of the total raffinate withdrawn during the 60 seconds would be withdrawn during the last 30 seconds of X, and more of the total raffinate would be withdrawn during the 60 seconds would be withdrawn during the first 30 seconds of X.

In a particular embodiment, at least 60% of the raffinate may be withdrawn from the SMB adsorptive separation apparatus during a time subinterval of from 0 to 40% of X (i.e., a time interval extending over the first 40% of X), and less than 40% of the raffinate may be withdrawn from the SMB adsorptive separation apparatus during a time subinterval of from 40 to 100% of X (i.e., a time interval extending from the end of the first 40% of X to the end of X). According to this embodiment, if X is 60 seconds, at least 60% of the raffinate would be withdrawn from the SMB adsorptive separation apparatus during the first 20 seconds of X, and less than 40% of the raffinate may be withdrawn from the SMB adsorptive separation apparatus during the last 40 seconds of X.

In another embodiment, the flow of raffinate may be described in terms of five (5) subintervals of X. In particular, (1) at least 25% of the raffinate, which is withdrawn in time interval X, may be withdrawn during a time subinterval of from 0 to 20% of X (i.e., a time interval extending over the first 20% of X); (2) at least 25% of the raffinate, which is withdrawn in time interval X, may be withdrawn during a time subinterval of from 20 to 40% of X (i.e., a time interval extending from the end of the first 20% of X to the end of the first 40% of X); (3) less than 15% of the raffinate, which is withdrawn in time interval X, may be withdrawn during a time subinterval of from 40 to 60% of X (i.e., a time interval extending from the end of the first 40% of X to the end of the first 60% of X); (4) less than 15% of the raffinate, which is withdrawn in time interval X, may be withdrawn during a time subinterval of from 60 to 80% of X (i.e., a time interval extending from the end of the first 60% of X to the end of the first 80% of X); and (5) less than 20% of the raffinate, which is withdrawn in time interval X, may be withdrawn during a time subinterval of from 80 to 100% of X (i.e., a time interval extending from the end of the first 80% of X to the end of X). According to this embodiment, if X is 60 seconds, (1) at least 25% of the raffinate, which is withdrawn in time interval X, would be withdrawn during the first 12 seconds of X; (2) at least 25% of the raffinate, which is withdrawn in time interval X, would be withdrawn during a time subinterval of from 12 to 24 seconds from the start of X; (3) less than 15% of the raffinate, which is withdrawn in time interval X, would be withdrawn during a time subinterval of from 24 to 36 seconds from the start of X; (4) less than 15% of the raffinate, which is withdrawn in time interval X, would be withdrawn during a time subinterval of from 36 to 48 seconds from the start of X, and (5) less than 15% of the raffinate, which is withdrawn in time interval X, would be withdrawn during a time subinterval of from 48 to 60 seconds from the start of X. After 60 seconds the flow of raffinate from a bed would be interrupted and resumed in the next bed downstream in terms of the flow of circulating fluid in the SMB adsorptive separation apparatus.

The flow rate of the extract stream may also be varied during time interval X. For example, less than 30% of the extract may be withdrawn from the SMB adsorptive separation apparatus or SMB adsorptive zone during a time subinterval of from 0 to 40% of X (i.e., a time interval extending over the first 40% of X), and at least 70% of the extract may be withdrawn from the SMB separation apparatus during a time subinterval of from 40 to 100% of X (i.e., a time interval extending from the end of the first 40% of X to the end of X). According to this embodiment, if X is 60 seconds, less than 30% of the extract would be withdrawn from the SMB adsorptive separation apparatus during the first 20 seconds of X, and at least 70% of the raffinate may be withdrawn from the SMB adsorptive separation apparatus during the last 40 seconds of X.

In another embodiment, the flow of extract may be described in terms of five (5) subintervals of X. In particular, (1) less than 15% of the extract, which is withdrawn in time interval X, may be withdrawn during a time subinterval of from 0 to 20% of X (i.e., a time interval extending over the first 20% of X); (2) less than 15% of the extract, which is withdrawn in time interval X, may be withdrawn during a time subinterval of from 20 to 40% of X (i.e., a time interval extending from the end of the first 20% of X to the end of the first 40% of X); (3) at least 15% of the extract, which is withdrawn in time interval X, may be withdrawn during a time subinterval of from 40 to 60% of X (i.e., a time interval extending from the end of the first 40% of X to the end of the first 60% of X); (4) at least 20% of the extract, which is withdrawn in time interval X, may be withdrawn during a time subinterval of from 60 to 80% of X (i.e., a time interval extending from the end of the first 60% of X to the end of the first 80% of X); and (5) at least 20% of the extract, which is withdrawn in time interval X, may be withdrawn during a time subinterval of from 80 to 100% of X (i.e., a time interval extending from the end of the first 80% of X to the end of X). According to this embodiment, if X is 60 seconds, (1) less than 15% of the extract, which is withdrawn in time interval X, would be withdrawn during the first 12 seconds of X; (2) less than 15% of the extract, which is withdrawn in time interval X, would be withdrawn during a time subinterval of from 12 to 24 seconds from the start of X; (3) at least 15% of the extract, which is withdrawn in time interval X, would be withdrawn during a time subinterval of from 24 to 36 seconds from the start of X; (4) at least 20% of the extract, which is withdrawn in time interval X, would be withdrawn during a time subinterval of from 36 to 48 seconds from the start of X, and (5) at least 20% of the extract, which is withdrawn in time interval X, would be withdrawn during a time subinterval of from 48 to 60 seconds from the start of X. After 60 seconds the flow of extract from a bed would be interrupted and resumed in the next bed downstream in terms of the flow of circulating fluid in the SMB adsorptive separation apparatus.

EXAMPLES

In the Examples that follow, a computer model is used to simulate the separation of PX from other $C_8$ aromatics in a Parex™ unit. The unit comprises two columns, as shown in FIG. 1, in fluid communication with a rotary valve device (not shown). Each column comprises twelve adsorbent bed chambers, stacked one on top of the other, containing an adsorbent. For the purposes of explanation, these beds are identified as beds 101 to 124. The number of beds described in each zone is for illustrative purposes and the number of beds may be varied without changing the concepts described herein.

In the first column, the beds are stacked such that fluid introduced into the top of the first column flows downward through the first bed (i.e., bed 101) and then through the beds below to the last bed (i.e., bed 112) in the first column. Fluid from the bottom of the first column then flows to the top of the second column where it flows downward through the beds (i.e., beds 113-124). Fluid from the bottom of the second column then flows to the top of the first column to complete a loop of circulating bulk fluid throughout the columns.

The initial introduction of feed may take place in any of the beds of the apparatus. For example, feed may be introduced to the first bed in the first column. The feed is primarily composed of $C_8$ aromatics having 23 percent PX and 77 percent of a mixture of MX, OX, and EB. The feed may also include small amounts of impurities including TOL and paraffins. The feed may be a mixture of product streams from a reforming process, a transalkylation process, and an isomerization process.

When a steady state operation of the SMB unit is achieved, the beds of the apparatus may be described in terms of four sub-zones, i.e., a desorption sub-zone, a purification or rectification sub-zone, an adsorption sub-zone, and a buffer sub-zone. In a standard SMB unit, (1) the desorption sub-zone may include the bed to which a desorbent stream is introduced and four beds downstream from this bed terminating in the bed from which the extract stream is withdrawn, (2) the purification sub-zone may include nine beds immediately downstream of desorption sub-zone, terminating with the bed immediately upstream from the bed to which feed is introduced, (3) the adsorption sub-zone may include the bed to which feed is introduced and six beds immediately downstream of the purification sub-zone terminating in the bed from which a raffinate stream is withdrawn, and (4) the buffer sub-zone may include six beds immediately downstream from the purification sub-zone and terminating in the bed immediately upstream from the desorption sub-zone. The number of beds in each zone may vary from the numbers described above.

The raffinate and extract streams may pass through conduits and through a rotary valve device. These streams may then be distilled to separate desorbent from $C_8$ aromatics. A PX product may be recovered from the distillation of the extract stream. MX, OX, and EB obtained by distillation of the raffinate stream may be passed to an isomerization unit to convert a portion of these $C_8$ aromatics to PX, and the isomerized $C_8$ aromatics may then be used as a portion of the feed to the adsorption process. Desorbent recovered by distillation of the extract and raffinate streams may be recycled to the adsorption process.

Parameters for Examples 1 and 2

In Examples 1 and 2 which follow, an SMB model that consists of 24 beds (length 1.135 m, cross-sectional area 13.3 m²) was employed. A mixture of $C_8$ aromatics PX, OX, MX, and EB) and desorbent (pDEB) was assumed to be fed to the unit.

The sub-zone configuration is consistent in this study. For an SMB with 24 beds, the sub-zone configuration is fixed to 6:9:6:3 (i.e., six beds between desorbent and extract, nine beds between extract and feed, six beds between feed and raffinate, and three bed between raffinate and desorbent). For SMBs with fewer numbers of beds, the ratio is kept as close as possible to 2:3:2:1; for example, for an SMB zone with 16 beds, the sub-zone configuration is 4:6:4:2.

Consistent with M. Minceva, and A. E. Rodrigues, 'Modeling and Simulation of a Simulated Moving Bed for the Separation of P-Xylene', *Industrial & Engineering Chemistry Research*, 41 (2002), 3454-61, the following assumptions are made: (1) isothermal, isobaric operation; (2) constant velocity within each zone; (3) solid phase concentration is homogeneous throughout adsorbent particles; and (4) the mass transfer between the liquid and adsorbent phases is described by the linear driving force (LDF) model.

Based on these assumptions, mass balance equations can be written as:

$$\frac{\partial C_{ik}(z,t)}{\partial t} - D_{ik}(t)\frac{\partial^2 C_{ik}(z,t)}{\partial z^2} - v_k^*(t)\frac{\partial C_{ik}(z,t)}{\partial z} - \frac{(1-\varepsilon)}{\varepsilon}\frac{\partial q_{ik}(z,t)}{\partial t}$$

where is the index for components (i=PX,MX,OX,EB, PDEB); k is the index for columns (k=1 ... $N_{bed}$, where $N_{bed}$ is the total number of beds): c is the bulk liquid concentration $$\left(\text{unit}\frac{kg}{m^3}\right);$$

q is the adsorbate concentration $$\left(\text{unit}\frac{kg}{m^3}\right);$$

$\varepsilon$ is the overall porosity; D is the axial dispersion coefficient; and $v_k^*$ is the interstitial velocity in columns This mass balance equation describes the change of bulk liquid concentration at a specific position inside of a column (first term) with respect to dispersion (second term), convection (third term), and adsorption/desorption process (fourth term).

The LDF model is written as:

$$\frac{\partial q_{ik}(z,t)}{\partial t} = k(q_{ik}^*(z,t) - q_{ik}(z,t))$$

where q is the adsorbate concentration in equilibrium with the liquid phase (unit $$\left(\text{unit}\frac{kg}{m^3}\right).$$

The LDF model describes the mass flux into the solid phase. The adsorbate concentration in equilibrium with the liquid phase can be obtained from an adsorption isotherm.

At the node between columns, the mass balance is calculated by subtracting outlet flow rates and adding inlet flow rates:

$$F_{k+1} = F_k + F_{Feed,k} + F_{desorbent,k} - F_{raffinate,k} - F_{extract,k}$$

For columns that are not connected to inlet or outlet streams, $F_{Feed,k}$ or $F_{desorbent,k}$ or $F_{raffinate,k}$ or $F_{extract,k}$ is zero.

The CSS constraints are given as:

$$C_{k+1}(z,t_{end}) = C_k(z,t_0)$$

where $t_{end}$ is the time at the end of a step, and $t_0$ is the beginning of a step. Here, stepwise symmetry is assumed, where every step is identical.

Model parameters were taken from the literature, in particular, from M. Minceva, and A. E. Rodrigues, 'Modeling and Simulation of a Simulated Moving Bed for the Separation of P-Xylene', *Industrial & Engineering Chemistry Research*, 41 (2002), 3454-61. Model parameters are summarized in Table 1.

TABLE 1

| SMB unit geometry | model parameter |
|---|---|
| $L_c$ = 113.5 cm | $Pe = v_k L_k / D_{Lk} = 2000$ |
| $d_c$ = 411.7 cm | $k = 2$ min$^{-1}$ |
| $V_c = 15.1 \times 10^6$ cm$^3$ | $d_p = 0.092$ cm |
| no. of columns = 24 | $\epsilon = 0.39$ |
| configuration = 6-9-6-3 | $p = 1.39$ g/cm$^3$ |
| | $q_{mPX(MX:OX:EB)} = 130.3$ mg/g |
| | $K_{PX} = 1.0658$ cm$^3$/mg |
| | $K_{MX} = 0.2299$ cm$^3$/mg |
| | $K_{OX} = 0.1884$ cm$^3$/mg |
| | $K_{EB} = 0.3067$ cm$^3$/mg |
| | $q_{mPOEB} = 107.7$ mg/g |
| | $K_{POEB} = 1.2935$ cm$^3$/mg |

The mass transfer coefficient was changed from 2 min$^{-1}$ to 0.75 min$^{-1}$.

The optimization problem was formulated as follows:
Objective function: maximize $F_{Feed}$
Decision variables: $F_1$, $F_2$, $F_3$, $F_4$, $t_{st}$
where $F_j$'s are zone flow rates, and $t_{st}$ is the step time
Main Constraint: Extract purity (PX)≥99.7%
Extract recovery (PX)≥97.0%

The model was discretized into a set of algebraic differential equations by applying the center finite difference method (CFDM) to the spatial domain and orthogonal collocation finite element method (OCFEM) to the temporal domain respectively. The discretized problem was solved by an interior-point optimization algorithm, IPOPT.

Example 1

This Example analyzes the effect of reducing the number of adsorbent beds in an SMB unit while maintaining constant total sieve volume in the unit in the separation of PX from mixed xylenes. SMB units having 8 adsorbent beds, 16 adsorbent beds, and the typical 24 adsorbent beds were used while overall amount of adsorbent in the unit was kept constant. Thus, for units with fewer beds, the beds are larger to contain more adsorbent volume. For example, when the number of beds was reduced from 24 to 8, the length of each bed was increased from 1.135 m to 3.405 m. For each unit, regardless of the number of adsorbent beds used, the total amount of adsorbent for cases is fixed.

The results of model-based SMB optimization are shown in Tables 2 and 3. Table 2 shows the optimized flow rates.

TABLE 2

| # of Beds | 8 | 16 | 24 |
|---|---|---|---|
| Substep 1 length (min) | 2.90 | 1.21 | 0.67 |
| Substep 2 length (min) | 3.25 | 1.69 | 1.24 |
| Substep 1 feed flow rate (m$^3$/min) | 0.00 | 0.00 | 0.00 |
| Substep 2 feed flow rate (m$^3$/min) | 4.29 | 4.03 | 3.62 |
| Substep 1 extract flow rate (m$^3$/min) | 0.00 | 0.00 | 0.00 |
| Substep 2 extract flow rate (m$^3$/min) | 6.77 | 6.49 | 6.20 |
| Substep 1 desorbent flow rate (m$^3$/min) | 5.85 | 6.32 | 6.97 |
| Substep 2 desorbent flow rate (m$^3$/min) | 3.65 | 3.41 | 3.67 |

TABLE 2-continued

| # of Beds | 8 | 16 | 24 |
|---|---|---|---|
| Substep 1 raffinate flow rate (m$^3$/min) | 5.85 | 6.32 | 6.97 |
| Substep 2 raffinate flow rate (m$^3$/min) | 1.18 | 0.96 | 1.08 |
| Substep 1 zone 1 flow rate (m$^3$/min) | 5.85 | 6.51 | 6.97 |
| Substep 2 zone 1 flow rate (m$^3$/min) | 8.50 | 8.50 | 8.50 |

Table 3 shows the effect of PowerFeed on the separation with differing numbers of adsorbent beds. It can be seen that PowerFeed effectively mitigates the performance deterioration associated with fewer numbers of beds.

TABLE 3

| # of Beds | Production without PowerFeed (m$^3$/min) | Production with PowerFeed (m$^3$/min) | Losses with reduced beds (without PowerFeed) | Losses with reduced beds (with PowerFeed) |
|---|---|---|---|---|
| 8 | 1.95 | 2.26 | 14% | 4% |
| 16 | 2.22 | 2.35 | 2% | 0% |
| 24 | 2.28 | 2.35 | — | — |

Using 24 beds without PowerFeed, a maximum feed flow rate of 2.28 m$^3$/min is achieved. When the number of beds was reduced from 24 to 8, the maximum feed flow rate was reduced from 2.28 to 1.95 m$^3$/min (a 16.5% loss). When PowerFeed is used, for a 24 bed unit, a maximum feed flow rate of 2.35 m$^3$/min is achieved. When the number of beds was reduced from 24 to 8 and PowerFeed used, the maximum feed flow rate remained a relatively high value of 2.26 m$^3$/min. This result shows that a similar throughput to that currently achieved by conventional units with 24 beds can be achieved using 8 beds with the same sieve volume when the PowerFeed process is used. Additionally, the conventional throughput can be raised by 3% by using PowerFeed with the traditional 24 beds.

Example 2

This Example analyzes the effect of reducing the number of adsorbent beds in an SMB unit while maintaining constant sieve volume per bed in the separation of PX from mixed xylenes. SMB units having 8 adsorbent beds, 12 adsorbent beds, 16 adsorbent beds, and the typical 24 adsorbent beds were used while the size and volume of each bed was held constant (1.135 m long). The PX purity in the extract was fixed to be 99.7%, and the PX recovery in the extract was fixed to be 97.0%. The optimization objective was to maximize the feed flow rate, which represents productivity.

Note that case studies 12a and 12b both represent a system with 12 beds, but have different sub-zone configurations since an SMB with 12 beds cannot have a sub-zone configuration of 2:3:2:1. Case 12a has a sub-zone configuration of 3:5:3:1, and case 12b has a sub-zone configuration of 3:4:3:2.

The results of model-based SMB optimization are shown in Tables 4 and 5. The optimized flow rates are shown in Table 4.

TABLE 4

| # of Beds | 8 | 12 | 12 | 16 | 24 |
|---|---|---|---|---|---|
| Case | 8 | 12a | 12b | 16 | 24 |
| Substep 1 length (min) | 3.13 | 2.06 | 2.45 | 1.49 | 0.67 |
| Substep 2 length (min) | 2.13 | 1.56 | 1.63 | 1.35 | 1.24 |

TABLE 4-continued

| # of Beds | 8 | 12 | 12 | 16 | 24 |
|---|---|---|---|---|---|
| Substep 1 feed flow rate (m³/min) | 0.00 | 0.00 | 0.00 | 0.00 | 0.00 |
| Substep 2 feed flow rate (m³/min) | 2.04 | 2.80 | 2.84 | 3.35 | 3.62 |
| Substep 1 extract flow rate (m³/min) | 0.00 | 0.00 | 0.00 | 0.00 | 0.00 |
| Substep 2 extract flow rate (m³/min) | 8.05 | 7.85 | 7.85 | 7.43 | 6.20 |
| Substep 1 desorbent flow rate (m³/min) | 2.10 | 3.16 | 2.65 | 4.08 | 6.97 |
| Substep 2 desorbent flow rate (m³/min) | 6.06 | 5.48 | 5.05 | 8.50 | 3.67 |
| Substep 1 raffinate flow rate (m³/min) | 2.10 | 3.16 | 2.65 | 3.76 | 6.97 |
| Substep 2 raffinate flow rate (m³/min) | 0.05 | 0.44 | 0.04 | 0.35 | 1.08 |
| Substep 1 zone 1 flow rate (m³/min) | 2.10 | 3.16 | 2.65 | 4.08 | 6.97 |
| Substep 2 zone 1 flow rate (m³/min) | 8.50 | 8.50 | 8.50 | 8.50 | 8.50 |

Table 5 shows the effect of PowerFeed on the separation with differing numbers of adsorbent beds having constant adsorbent volume per bed.

TABLE 5

| # of Beds | Case | Production without PowerFeed (m³/min) | Production with PowerFeed (m³/min) | Losses with reduced beds (without PowerFeed) | Losses with reduced beds (with PowerFeed) |
|---|---|---|---|---|---|
| 8 | 8 | 0.63 | 0.75 | 72% | 68% |
| 12 | 12a | 1.10 | 1.21 | 52% | 48% |
| 12 | 12b | 1.01 | 1.14 | 55% | 52% |
| 16 | 16 | 1.48 | 1.58 | 35% | 33% |
| 24 | 24 | 2.28 | 2.35 | — | — |

The decrease in maximum feed flow rate was large as the number of beds was reduced. Since the length of each bed was fixed to be 1.135 m, and fewer number of beds means a smaller amount of total adsorbent available in the SMB, then the volume of xylenes that can be successfully separated is reduced. When the number of beds was reduced from 24 to 8 and PowerFeed was not used, the maximum feed flow rate was reduced dramatically from 2.28 to 0.63 m³/min. When PowerFeed is used, the maximum feed flow rate is consistently increased by about 0.10 m³/min for each case. When 8 beds and PowerFeed is used, the maximum feed flow rate is increased from 0.63 to 0.75 m³/min, which is about a 15% improvement.

The results for Table 5 were compared on a per-kg-sieve basis to study the adsorbent efficiency by calculating the normalized feed flow rate (dividing the maximum feed flow rate by the total weight of sieve in kg) in each case. The results are shown below in Table 6. The normalized feed flow rate without PowerFeed decreased by 17.0% as the number of beds decreased from 24 to 8, indicating the adsorbent is less efficient in the 8-bed system. With the implementation of PowerFeed, the decrease in normalized feed flow rate was less than 3.9%, indicating that the PowerFeed increases adsorbent efficiency compared to the conventional, constant-flow alternative. An SMB with the sub-zone configuration used in case 12a has the maximum normalized feed flow rate—even surpassing that of the 24-bed SMB with PowerFeed.

TABLE 6

| # of Beds | Case | Normalized Throughput without PowerFeed (kg-feed/kg-sieve/hr) | Normalized Throughput with PowerFeed (kg-feed/kg-sieve/hr) | Losses with reduced beds (without PowerFeed) | Losses with reduced beds (with PowerFeed) |
|---|---|---|---|---|---|
| 8 | 8 | 0.284 | 0.339 | 17% | 3.9% |
| 12 | 12a | 0.331 | 0.363 | 3% | −3.0% |
| 12 | 12b | 0.305 | 0.341 | 11% | 3.2% |
| 16 | 16 | 0.333 | 0.356 | 3% | −1.0% |
| 24 | 24 | 0.342 | 0.353 | — | — |

Example 3

This Example analyzes the effect of reducing the number of adsorbent beds in an SMB unit while maintaining constant sieve volume per bed in the separation of EB from MX and OX. The same model (with isotherm parameters taken from Silva et al. Chemical *Engineering & Technology*, 37 (2014) 1541-1551 in this case) was used to explore the impact of PowerFeed on throughput for EB extraction from the raffinate stream (18% EB, 65% MX 1% PX and 16% OX) from the examples above. SMB units having 8 adsorbent beds, 12 adsorbent beds, 16 adsorbent beds, and the typical 24 adsorbent beds were used while the size and volume of each bed was held constant (1.135 m long). The EB purity in the extract was constrained to 80% and the recovery was also constrained to 80%. Results are shown in Table 7.

Note that case studies 12a and 12b both represent a system with 12 beds, but have different sub-zone configurations since an SMB with 12 beds cannot have a sub-zone configuration of 2:3:2:1. Case 12a has a sub-zone configuration of 3:5:3:1, and case 12b has a sub-zone configuration of 3:4:3:2.

TABLE 7

| # of Beds | Case | Normalized Throughput without PowerFeed (kg-feed/kg-sieve/hr) | Normalized Throughput with PowerFeed (kg-feed/kg-sieve/hr) |
|---|---|---|---|
| 8 | 8 | 0.284 | 0.339 |
| 12 | 12a | 0.331 | 0.363 |
| 12 | 12b | 0.305 | 0.341 |
| 16 | 16 | 0.333 | 0.356 |
| 24 | 24 | 0.342 | 0.353 |

As is seen in Table 7, a higher increase in total throughput using 2-substep PowerFeed versus no PowerFeed is shown with a lower number of beds. Thus, fewer beds are required to meet similar performance objectives when PowerFeed is applied in the separation of EB from MX and OX.

While particular embodiments have been described and illustrated herein, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for separating paraxylene and at least one other $C_8$ aromatic from a mixture of paraxylene (PX), metaxylene (MX), orthoxylene (OX), and ethylbenzene (EB) in a simulated moving bed adsorption apparatus having 24 adsorbent beds in two columns, wherein each column contains 12 adsorbent beds, and wherein the 24 absorbent beds comprise a first absorption zone containing 8 to 16 absorbent beds and a second absorption zone containing the balance of the 24 adsorbent beds, wherein each adsorption zone performs a different separation and contained in a single column or span both columns;

wherein PX is separated from the mixture in the first adsorption zone to produce a raffinate comprising MX, OX, and EB, and separating at least one of MX, OX, and EB from the raffinate in the second adsorption zone;

wherein a first feed stream and a first desorbent stream are introduced into the first adsorption zone, wherein a first extract stream and a first raffinate stream are withdrawn from the first adsorption zone, wherein a second feed stream and a second desorbent stream are introduced into the second adsorption zone, wherein a second extract stream and a second raffinate stream are withdrawn from the second adsorption zone, wherein the second feed stream comprises at least a portion of the first raffinate; and wherein the flow rate of at least one of the streams introduced into or withdrawn from the first adsorption zone is varied during a step time of interval X.

2. The process of claim 1, wherein the first adsorption zone contains 12 adsorbent beds contained within one column and the second adsorption zone contains 12 adsorbent beds contained within the other column, the first and second adsorption zones are separate and distinct, and the only fluid communication between the two columns is the introduction of at least a portion of the first raffinate as the second feed stream.

3. The process of claim 1, wherein the first adsorption zone comprises 8 adsorbent beds and the second adsorption zone comprises 16 adsorbent beds.

4. The process of claim 1, wherein the first adsorption zone comprises 16 adsorbent beds and the second adsorption zone comprises 8 adsorbent beds.

5. The process of claim 3, wherein the first and second adsorption zones are separate and distinct and the only fluid communication between the first and second adsorption zones is the introduction of at least a portion of the first raffinate as the second feed stream.

6. The process of claim 4, wherein the first adsorption zone comprises:
a first adsorption sub-zone which includes the adsorbent beds between the first feed introduction point and the first raffinate withdrawal point;
a first purification sub-zone which includes the adsorbent beds between the first extract withdrawal point and the first feed introduction point;
a first desorption sub-zone which includes the adsorbent beds between the first desorbent introduction point and the first extract withdrawal point; and
a first buffer sub-zone which includes the beds between the first raffinate withdrawal point and the first desorbent introduction point;
wherein the second adsorption zone is positioned within the first buffer sub-zone.

7. A process for separating paraxylene (PX) and at least one other $C_8$ aromatic from a mixture comprising $C_8$ aromatics in a simulated moving bed adsorption apparatus comprising 24 adsorbent beds in two columns, each column comprising 12 adsorbent beds, wherein the 24 absorbent beds comprise a first absorption zone containing 8 to 16 absorbent beds and a second absorption zone containing the balance of the 24 adsorbent beds, and wherein each adsorption zone performs a different separation and may be contained in a single column or span both columns, the process comprising the steps of:

(a) introducing a first feed stream into the first adsorption zone of the simulated moving bed adsorption apparatus, wherein the first feed stream comprises a mixture of PX, metaxylene (MX), orthoxylene (OX), and ethylbenzene (EB);

(b) introducing a first desorbent stream into the first adsorption zone, wherein the first desorbent stream comprises desorbent;

(c) withdrawing a first extract stream from the first adsorption zone, wherein the first extract stream comprises desorbent and PX;

(d) withdrawing a first raffinate stream from the first adsorption zone, wherein the first raffinate stream comprises desorbent, MX, OX, and EB;

(e) maintaining a flow of circulating fluid throughout the first adsorption zone;

(f) switching the flow of streams into and out of the first adsorption zone to a bed downstream in terms of the direction of the circulating fluid at a step time interval X;

wherein the flow rate of at least one of the first feed stream, first desorbent stream, first extract stream, and first raffinate stream is varied during the step time interval X;

(g) introducing a second feed stream into the second adsorption zone of the simulated moving bed adsorption apparatus, wherein the second feed stream comprises at least a portion of the first raffinate stream of step (d);

(h) introducing a second desorbent stream into the second adsorption zone, wherein the second desorbent stream comprises desorbent;

(i) withdrawing a second extract stream from the second adsorption zone, wherein the second extract stream comprises desorbent and a $C_8$ aromatic selected from the group consisting of MX, OX, and EB;

(j) withdrawing a second raffinate stream from the second adsorption zone, wherein the second raffinate stream comprises desorbent and the two $C_8$ aromatics not contained in the extract stream of step (i);

(k) maintaining a flow of circulating fluid throughout the second adsorption zone; and (l) switching the flow of streams into and out of the second adsorption zone to a bed downstream in terms of the direction of the circulating fluid at a step time interval Y, which may be the same as or different than the step time interval X.

8. The process of claim 7, wherein the first adsorption zone comprises 12 adsorbent beds contained within one column and the second adsorption zone comprises 12 adsorbent beds contained within the other column, the first and second adsorption zones are separate and distinct, and the only fluid communication between the two columns is the introduction of at least a portion of the first raffinate as the second feed stream.

9. The process of claim 7, wherein the first adsorption zone comprises 8 adsorbent beds and the second adsorption zone comprises 16 adsorbent beds.

10. The process of claim 7, wherein the first adsorption zone comprises 16 adsorbent beds and the second adsorption zone comprises 8 adsorbent beds.

11. The process of claim 9, wherein the first and second adsorption zones are separate and distinct and the only fluid communication between the first and second adsorption zones is the introduction of at least a portion of the first raffinate as the second feed stream.

12. The process of claim 10, wherein the first adsorption zone comprises:
a first adsorption sub-zone which includes the adsorbent beds between the first feed introduction point and the first raffinate withdrawal point;
a first purification sub-zone which includes the adsorbent beds between the first extract withdrawal point and the first feed introduction point;
a first desorption sub-zone which includes the adsorbent beds between the first desorbent introduction point and the first extract withdrawal point; and
a first buffer sub-zone which includes the beds between the first raffinate withdrawal point and the first desorbent introduction point;
wherein the second adsorption zone is positioned within the first buffer sub-zone.

13. The process of claim 9, wherein the first and second adsorption zones are separate and distinct and wherein the first adsorption zone comprises:
a first adsorption sub-zone which includes the adsorbent beds between the first feed introduction point and the first raffinate withdrawal point;
a first purification sub-zone which includes the adsorbent beds between the first extract withdrawal point and the first feed introduction point;
a first desorption sub-zone which includes the adsorbent beds between the first desorbent introduction point and the first extract withdrawal point; and
a first buffer sub-zone which includes the beds between the first raffinate withdrawal point and the first desorbent introduction point;
wherein the second adsorption zone comprises:
a second adsorption sub-zone which includes the adsorbent beds between the second feed introduction point and the second raffinate withdrawal point;
a second purification sub-zone which includes the adsorbent beds between the second extract withdrawal point and the second feed introduction point;
a second desorption sub-zone which includes the adsorbent beds between the second desorbent introduction point and the second extract withdrawal point; and
a second buffer sub-zone which includes the beds between the second raffinate withdrawal point and the first desorbent introduction point; and
further wherein the sub-zone configuration, which is the number of adsorbent beds in the adsorption sub-zone: number of adsorbent beds in the purification sub-zone: number of adsorbent beds in the desorption sub-zone: number of adsorbent beds in the buffer sub-zone, is 2:3:2:1 in both the first and second adsorption zones.

14. The process of claim 8, wherein the first and second adsorption zones are separate and distinct and wherein the first adsorption zone comprises:
a first adsorption sub-zone which includes the adsorbent beds between the first feed introduction point and the first raffinate withdrawal point;
a first purification sub-zone which includes the adsorbent beds between the first extract withdrawal point and the first feed introduction point;
a first desorption sub-zone which includes the adsorbent beds between the first desorbent introduction point and the first extract withdrawal point; and
a first buffer sub-zone which includes the beds between the first raffinate withdrawal point and the first desorbent introduction point; and wherein the second adsorption zone comprises:
a second adsorption sub-zone which includes the adsorbent beds between the second feed introduction point and the second raffinate withdrawal point;
a second purification sub-zone which includes the adsorbent beds between the second extract withdrawal point and the second feed introduction point;
a second desorption sub-zone which includes the adsorbent beds between the second desorbent introduction point and the second extract withdrawal point; and
a second buffer sub-zone which includes the beds between the second raffinate withdrawal point and the first desorbent introduction point; and
further wherein the sub-zone configuration, which is the number of adsorbent beds in the adsorption sub-zone: number of adsorbent beds in the purification sub-zone: number of adsorbent beds in the desorption sub-zone: number of adsorbent beds in the buffer sub-zone, is 3:5:3:1 in both the first and second adsorption zones.

15. The process of claim 7, wherein desorbent is removed from the first raffinate stream before $C_8$ aromatics from the first raffinate are passed as the second feed stream to the second adsorption zone.

16. The process of claim 7, wherein desorbent is not removed from the first raffinate stream before $C_8$ aromatics from the first raffinate stream are passed as the second feed stream to the second adsorption zone.

17. The process of claim 7, wherein more of the first feed stream is introduced into the first adsorption first during a latter portion of the step time interval X than in an earlier portion of the step time interval X.

18. The process of claim 17, wherein less than 30% of the first feed stream is introduced into the first adsorption zone during a time subinterval of from 0 to 40% of the step time interval X; and
wherein at least 70% of the first feed stream is introduced into the first adsorption zone during a time subinterval of from 40 to 100% of the step time interval X.

19. The process of claim 17 or 18, wherein less than 10% of the first feed stream, which is introduced in the step time interval X, is introduced during a time subinterval of from 0 to 20% of the step time interval X;
wherein less than 15% of the first feed stream, which is introduced in the step time interval X, is introduced during a time subinterval of from 20 to 40% of the step time interval X;
wherein at least 15% of the first feed stream, which is introduced in the step time interval X, is introduced during a time subinterval of from 40 to 60% of the step time interval X;
wherein at least 20% of the first feed stream, which is introduced in the step time interval X, is introduced during a time subinterval of from 60 to 80% of the step time interval X; and
wherein at least 20% of the first feed stream, which is introduced in the step time interval X, is introduced during a time subinterval of from 80 to 100% of the step time interval X.

20. The process of claim 17, wherein less of the first raffinate stream is withdrawn from the first adsorption zone during the latter portion of the step time interval X than in the earlier portion of the step time interval X.

21. The process of claim 20, wherein at least 60% of the first raffinate stream is withdrawn from the first adsorption zone during a time subinterval of from 0 to 40% of the step time interval X, and wherein less than 40% of the first raffinate stream is withdrawn from the first adsorption zone during a time subinterval of from 40 to 100% of the step time interval X.

22. The process of claim 20, wherein at least 25% of the first raffinate stream, which is withdrawn in the step time interval X, is withdrawn during a time subinterval of from 0 to 20% of the step time interval X,
  wherein at least 25% of the first raffinate stream, which is withdrawn in the step time interval X, is withdrawn during a time subinterval of from 20 to 40% of the step time interval X,
  wherein less than 15% of the first raffinate stream, which is withdrawn in the step time interval X, is withdrawn during a time subinterval of from 40 to 60% of the step time interval X,
  wherein less than 15% of the first raffinate stream, which is withdrawn in the step time interval X, is withdrawn during a time subinterval of from 60 to 80% of the step time interval X, and
  wherein less than 20% of the first raffinate stream, which is withdrawn in the step time interval X, is withdrawn during a time subinterval of from 80 to 100% of the step time interval X.

23. The process of claim 17, wherein more of the first extract stream is withdrawn from the first adsorption zone during a latter portion of the step time interval X than in an earlier portion of the step time interval X.

24. The process of claim 23, wherein less than 30% of the first extract stream is withdrawn from the first adsorption zone during a time subinterval of from 0 to 40% of the step time interval X, and
  wherein at least 70% of the first extract stream is withdrawn from the first adsorption zone during a time subinterval of from 40 to 100% of the step time interval X.

25. The process of claim 23, wherein less than 15% of the first extract stream, which is withdrawn in the step time interval X, is withdrawn during a time subinterval of from 0 to 20% of the step time interval X,
  wherein less than 15% of the first extract stream, which is withdrawn in the step time interval X, is withdrawn during a time subinterval of from 20 to 40% of the step time interval X,
  wherein at least 15% of the first extract stream, which is withdrawn in the step time interval X, is withdrawn during a time subinterval of from 40 to 60% of the step time interval X,
  wherein at least 20% of the first extract stream, which is withdrawn in the step time interval X, is withdrawn during a time subinterval of from 60 to 80% of the step time interval X, and
  wherein at least 20% of the first extract stream, which is withdrawn in the step time interval X, is withdrawn during a time subinterval of from 80 to 100% of the step time interval X.

* * * * *